(12) United States Patent
Cha et al.

(10) Patent No.: US 7,622,550 B2
(45) Date of Patent: Nov. 24, 2009

(54) MUSSEL BIOADHESIVE

(75) Inventors: Hyung Joon Cha, Pohang (KR); Dong Soo Hwang, Pohang (KR)

(73) Assignees: Postech Foundation, Pohang, Kyungsangbuk-Do (KR); POSCO, Pohang-Shi, Kyungsangbuk-Do (KR)

( * ) Notice: Subject to any disclaimer, the term of this patent is extended or adjusted under 35 U.S.C. 154(b) by 359 days.

(21) Appl. No.: 10/599,313

(22) PCT Filed: Mar. 25, 2005

(86) PCT No.: PCT/KR2005/000888

§ 371 (c)(1),
(2), (4) Date: Sep. 25, 2006

(87) PCT Pub. No.: WO2005/092920

PCT Pub. Date: Oct. 6, 2005

(65) Prior Publication Data

US 2009/0151600 A1 Jun. 18, 2009

(51) Int. Cl.
- C07K 14/00 (2006.01)
- C07K 7/00 (2006.01)
- C07K 1/00 (2006.01)
- C09J 189/00 (2006.01)

(52) U.S. Cl. .................. 530/324; 530/300; 530/325
(58) Field of Classification Search .................. None
See application file for complete search history.

(56) References Cited

U.S. PATENT DOCUMENTS

| 5,015,677 A | 5/1991 | Benedict et al. |
| 5,202,236 A | 4/1993 | Maugh et al. |
| 2003/0065060 A1 | 4/2003 | Qvist et al. |

FOREIGN PATENT DOCUMENTS

| JP | 08-266281 | 10/1996 |
| WO | WO 97/10341 | 3/1997 |
| WO | WO 00/15789 | 3/2000 |
| WO | WO 01/44401 A1 | 6/2001 |

OTHER PUBLICATIONS

GenBank Accession No. ABM97415, pp. 1-2. Accessed Feb. 24, 2009.*
GenBank Accession No. AAX23972, pp. 1-2. Accessed Feb. 24, 2009.*
GenBank Accession No. AAX23969, pp. 1-2. Accessed Feb. 24, 2009.*
GenBank Accession No. CAA35954, pp. 1-2. Accessed Feb. 24, 2009.*
GenBank Accession No. AAA98797, pp. 1-3. Accessed Feb. 24, 2009.*
NCBI Accession No. AAS00463, Feb. 1, 2004.
Deming, T.J, "Mussel Byssus and biomolecular materials", Current Opinion in Chemical Biology (1999), 3: 100-105.
Database GenPept [Online] Jan. 24, 2007, "Adhesive Plaque Protein", BAA09851, retrieved from NCBI Sequence Viewer.
Database GenePept [Online] Jan. 24, 2003, "Adhesive Plaque Matrix Protein", BAA09850, retrieved from NCBI Sequence Viewer.
Hwang et al., "Cloning and expression of novel mussel adhesive protein from *Mytilus galloprovincialis*", Biomolecular Engineering (2003), 20(2):79.
Database Geneseq [Online] May 9, 2001, "Repetitive protein polymer protein sequence #76", XP002432105 retrieved from EBI accession No. GSN. AAB72776.
Database UniProt [Online] Mar. 1, 2002, "Polyphenolic phosphoprotein mefp-5 precursor", XP002432106 retrieved from EBI accession No. UNIPROT: Q8WTE8.
Database Geneseq [Online] Sep. 26, 2001, "Mussel adhesive derived peptide #2", XP002432107 retrieved from EBI accession No. GSN:AAG65052.
Database Geneseq [Online] Oct. 21, 2002, "Glue protein repeat unit", XP002432108 retrieved from EBI accession No. GSN: ABG69216.
Database Geneseq [Online] Sep. 9, 2004, "Mgfp-5 amino acid sequence, seq id 4", XP002432109 retrieved from EBI accession No. GSP: ADQ78274.
Waite et al., "Polyphosphoprotein from the adhesive pads of *Mytilus edulis*", Biochemistry (2001), 40(9):2887-2893.
Hwang et al., "Expression of functional recombinant mussel adhesive protein Mgfp-5 in *Escherichia coli*", Applied and Environmental Microbiology (2004), 70(6):3352-3359.

* cited by examiner

*Primary Examiner*—Cecilia Tsang
*Assistant Examiner*—Julie Ha
(74) *Attorney, Agent, or Firm*—Joseph Hyosuk Kim; JHK Law

(57) ABSTRACT

The present invention relates to a bioadhesive derived from mussel. In particular, it relates to a novel *Mytilus galloprovincialis* foot protein type 5 (MGFP-5) and a recombinant protein that is a hybrid of MGFP-5 and foot protein type 1 (FP-1), where an adhesive protein with adhesive activity can be economically mass-produced to be used in place of chemical adhesives through the present invention.

13 Claims, 27 Drawing Sheets

(A) Mgfp-151

(B) Mgfp-5

Mgfp-151 10000X

Mgfp-5 10000X

US 7,622,550 B2

MUSSEL BIOADHESIVE

BACKGROUND OF THE INVENTION

1. Field of the Invention

The present invention relates to a bio-adhesive derived from mussel, and more particularly to a novel *Mytilus galloprovincialis* foot protein-5 (MGFP-5) and a recombinant protein that is a hybrid of MGFP-5 and foot protein-1 (FP-1).

2. Background of the Invention

Mussels produce and secrete specialized water-resistant bioadhesives, and have been studied as a potential source of water-resistant bioadhesives. They adhere tightly to surfaces underwater using the byssus secreted from the foot of the mussel. At the end of each thread is an adhesive plaque containing a water-resistant glue that enables the plaque to anchor to wet solid surfaces (Waite, J. H., *Biology Review.* 58:209-231 (1983). This strong and water-insoluble adhesion has attracted interest for potential use in biotechnological applications. Mussel adhesive proteins can also be used as medical adhesives as they are non-toxic to the human body and do not impose immunogenicity (Dove et al., *Journal of American Dental Association.* 112:879 (1986)). Moreover, their biodegradable properties make them environmentally friendly.

The byssus can be divided into distal and proximal parts. The proximal part is connected to the stem gland of the mussel foot, while the distal part is connected to the adhesive plaques. The adhesive plaque is composed of five distinct types of proteins: foot protein type 1 (FP-1) to type 5 (FP-5) (Deming, T. J., *Current Opinion in Chemical Biology.* 3:100-105 (1999)).

All of the mussel adhesive proteins contain high ratios of 3,4-dihydroxyphenyl-L-alanine (DOPA), which is derived from hydroxylation of tyrosine residues (Waite, J. H., *Biology Review.* 58:209-231 (1983)). The adhesive proteins closest to the adhesion interface have the highest proportion of DOPA residues (Waite, J. H., *Integr. Comp. Biol.* 42:1172-1180 (2002)). In contrast, mussel adhesive protein analogs lacking DOPA show greatly reduced adhesion abilities (Yu et al., *Journal of American Chemical Society.* 121:5825-5826 (1999)). Indeed, a biochemical study showed that DOPA residues can enable mussel adhesive protein molecules to cross-link with each other via oxidative conversion to o-quinone. Thus, the DOPA content of a mussel adhesive protein appears to be specifically related to its adhesive properties.

Currently Cell-Tak, a naturally extracted mussel adhesive protein product, is commercially available. This adhesive is mainly composed of FP-1 and FP-2 type proteins, with a minor portion of FP-3. However, the natural extraction process is labor-intensive and inefficient, requiring around 10,000 mussels for 1 mg of protein (Morgan, D., *The Scientist.* 4:1-6 (1990)).

Therefore, researchers have sought to produce recombinant mussel adhesive proteins, for example FP-1, in expression systems such as *Escherichia coli* and yeast. However, these previous studies failed to express functional and economical mussel adhesive proteins due to a number of complications, including a highly biased amino acid composition (5 amino acid types comprise ~89% of the total amino acids in FP-1), different codon usage preferences between mussel and other expression systems (tRNA utilization problems) and low protein yields (U.S. Pat. No. 5,242,808, Filpula et al., *Biotechnol. Prog.* 6:171-177 (1990), Salerno et al., *Applied Microbiology and Biotechnology* 58:209-214 (1993), Kitamura et al., *Journal of Polymer Science Part A: Polymer Chemistry,* 37:729-736 (1999)).

SUMMARY OF THE INVENTION

An objective of the present invention is to provide a novel adhesive protein gene from mussel and to overcome the aforementioned problems in the prior art.

Another objective of the present invention is to provide a novel adhesive protein from mussel.

Another objective of the present invention is to provide a method for mass-producing a mussel adhesive protein in a biologically active form.

Another objective of the present invention is to provide a recombinant adhesive protein that is a fusion of two or more adhesive proteins from mussel.

Another objective of the present invention is to provide an adhesive that contains a novel adhesive protein as an active component.

The present invention provides a novel adhesive protein extracted from *Mytilus galloprovincialis* and a polynucleotide encoding the protein. The above adhesive protein preferably comprises the amino acid sequence shown in SEQ ID NO: 6. An example of the above polynucleotide is the nucleotide sequence shown in SEQ ID NO: 5.

The present invention also provides a recombinant adhesive protein where some amino acid sequences from FP-1 is attached to the amino- and/or carboxy-termini of a mussel adhesive protein, and a polynucleotide encoding the recombinant adhesive protein. An example of the recombinant adhesive protein is an amino acid sequence selected from the group consisting of the amino acid sequence shown in SEQ ID NO: 10, the amino acid sequence shown in SEQ ID NO: 12, the amino acid sequence shown in SEQ ID NO: 14, the amino acid sequence shown in SEQ ID NO: 18, the amino acid sequence shown in SEQ ID NO: 20, and the amino acid sequence shown in SEQ ID NO: 22. An example of the nucleotide sequence encoding the recombinant adhesive protein is the nucleotide sequence shown in SEQ ID NO: 9, the nucleotide sequence shown in SEQ ID NO: 11, the nucleotide sequence shown in SEQ ID NO: 13, the nucleotide sequence shown in SEQ ID NO: 17, the nucleotide sequence shown in SEQ ID NO: 19, and the nucleotide sequence shown in SEQ ID NO: 21.

The present invention also provides a vector which contains operably a nucleotide sequence encoding an adhesive protein.

The present invention also provides a transformant which contains operably a nucleotide sequence encoding an adhesive protein.

The present invention also provides a method of producing an adhesive protein which comprises the steps of:
  (a) constructing a vector which contains operably a nucleotide sequence encoding an adhesive protein;
  (b) constructing a transformant by transforming a host cell with the vector; and
  (c) producing a recombinant adhesive protein by culturing the transformant.

The present invention also provides a method of purifying an adhesive protein which comprises the steps of:
  (a) lysing the transformants, and then centrifuging it to separate the supernatant and the pellet;
  (b) making a suspension by adding an acidic organic solvent to the pellet; and
  (c) centrifuging the suspension to separate the supernatant.

The present invention also provides an adhesive containing an adhesive protein as the active component.

The present invention also provides a method of adjusting the adhesive property of an adhesive comprising controlling the concentration of an adhesive protein which is an active component of the aforementioned adhesive, or treating the adhesive with one or more material selected from the group consisting of oxidant, filler and surfactant.

The present invention also provides a coating material containing an adhesive protein as an active component.

DETAILED DESCRIPTION OF THE PREFERRED EMBODIMENTS

Figure 1:
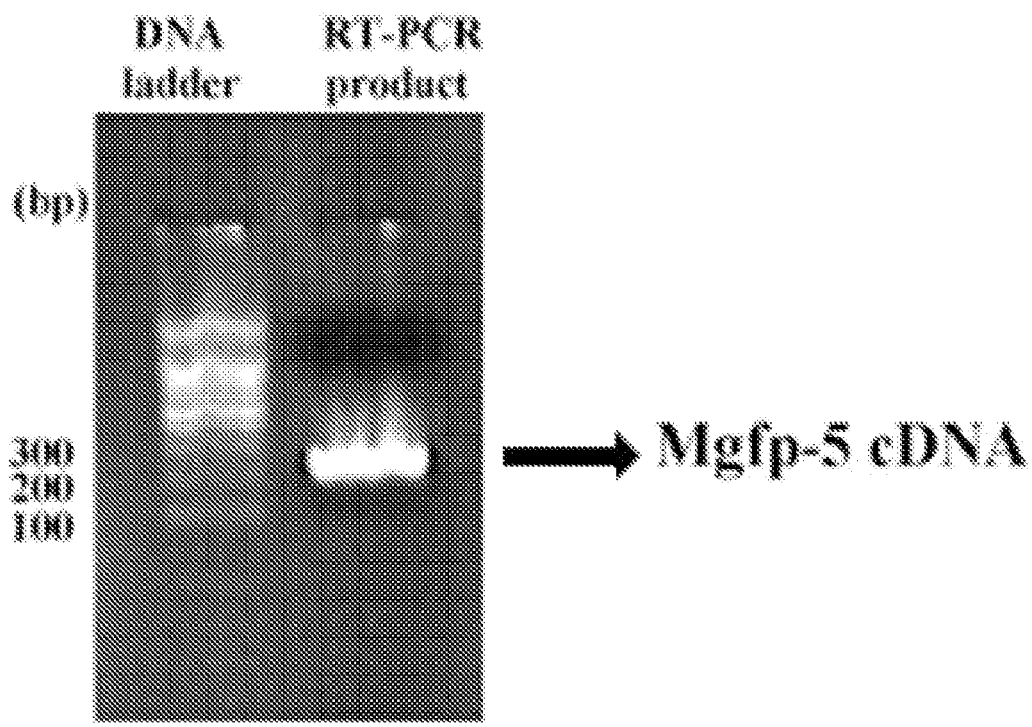
FIG. 1 is a picture of the electrophoresis of MGFP-5 cDNA fragments obtained by RT-PCR with RNA extracted from *Mytilus galloprovincialis* as the template.
Figure 2:
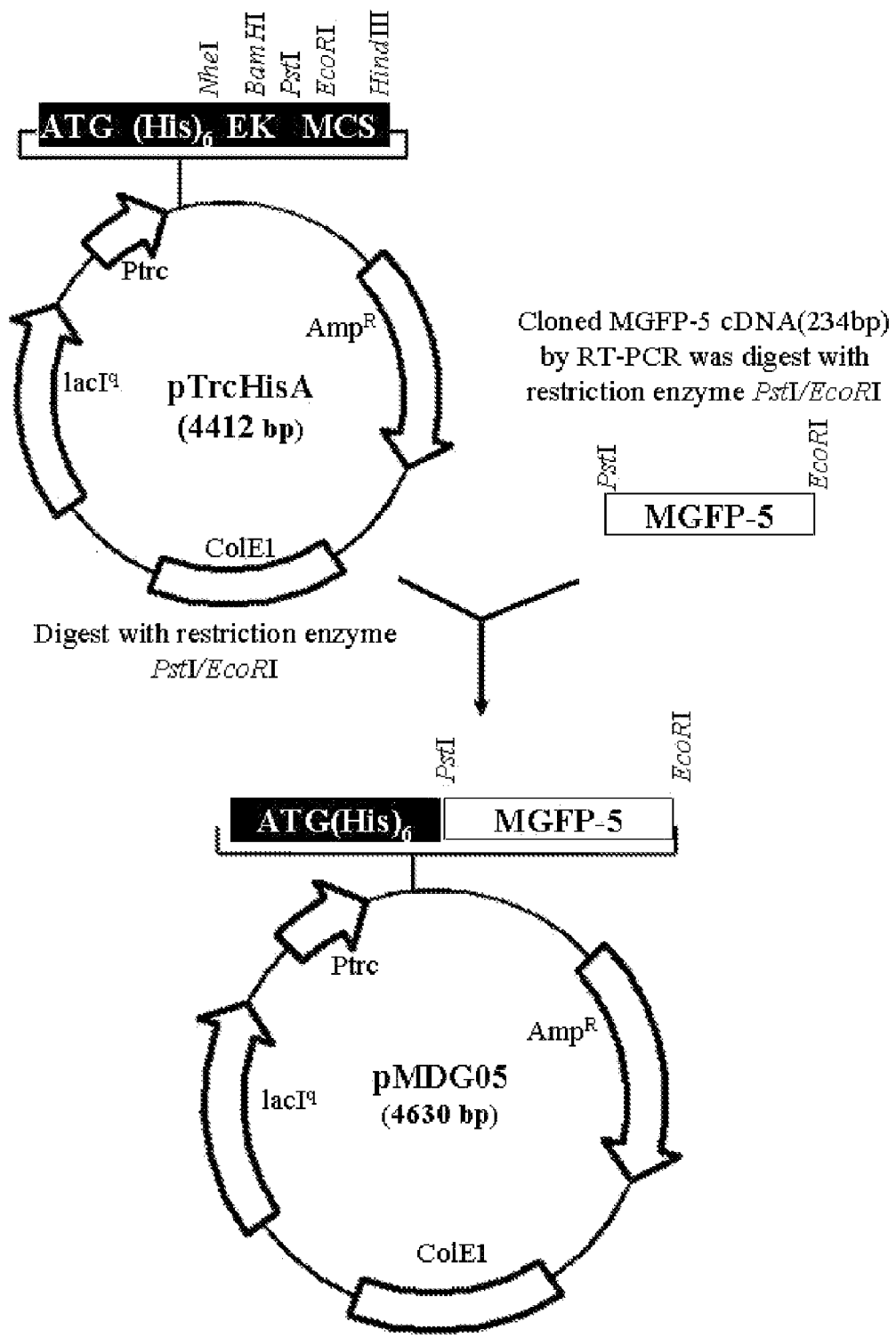
FIG. 2 shows the procedure for inserting MGFP-5 cDNA into a pTrcHis vector to construct a pMDG05 vector.

The inventors of the present invention have obtained a novel adhesion protein and its encoding gene from a type of mussel, *Mytilus galloprovincialis*, and they have established a system for the production of an adhesion protein that is translated from it. They have also established a recombinant adhesion protein that is a fusion of two or more mussel adhesion proteins, and a system for its production.

The adhesive protein of the present invention has the characteristic of attaching to a wide variety of substrates such as glass, metal, polymer resin, plastic or biological cell membranes such as prokaryotic membranes, eukaryotic membranes, and plant cell walls and lipids.

The adhesive protein of the present invention has at least 50% homology with the amino acid sequence shown in SEQ ID NO: 6, preferably 80%, more preferably 90%, and most preferably at least 95% homology, and at the same time can include amino acid sequences that have adhesive property, for example adhesive property that is similar to the amino acid sequence shown in SEQ ID NO: 6, or amino acid sequences that have 70 to 200% of the adhesive activity of the above.

For example, there is a protein that contains the amino acid sequence shown in SEQ ID NO: 6. An adhesive protein that contains the amino acid sequence as shown in the above SEQ ID NO: 6 is referred to as "MGFP-5" (*Mytilus galloprovincialis* foot protein type 5) from hereon.

A nucleotide encoding MGFP-5 can be expressed as a variety of nucleotide sequences depending on the amino acid codon usage, such as the nucleotide sequences shown in SEQ ID NO: 5 and SEQ ID NO: 15.

Also, the adhesive protein of the present invention can further contain a peptide at the amino- and/or carboxy-termini in order to improve the physicochemical properties of the adhesive protein. The above peptide may be added for the purpose of improving for example, the solubility, adhesion force, degree of crosslinking, and the degree of expression, purification, and recovery of protein. For example, the above peptide can be a general reporter protein such as GST or a histidine tag for the purpose of improving the purification.

An example of a form where a peptide is further included for the purpose of purifying an adhesive protein is a protein containing the amino acid sequence shown in SEQ ID NO: 16.

The above peptide preferably contains an amino acid sequence derived from an adhesive protein, and more preferably contains an amino acid sequence derived from a mussel adhesive protein. An example of the peptide is the amino acid sequence shown in SEQ ID NO: 25 is repeated 1 to 10 times in tandem. In an embodiment of the present invention, a SEQ ID NO: 8 was constructed in which the amino acid sequence shown in SEQ ID NO: 25 is repeated 6 times in tandem, and attached to the amino- and/or carboxy-termini of the adhesive protein in the present invention. The amino acid sequence shown in the SEQ ID NO: 25 is a part of the sequence of the FP-1 protein.

Examples of recombinant adhesive proteins where the sequence shown in SEQ ID NO: 25 is additionally attached, are amino acid sequences shown in SEQ ID Nos: 10, 12, and 14. The SEQ ID NO: 10 is where the sequence shown in SEQ ID NO: 25 is repeated 6 times in tandem and attached to the amino-terminus of the amino acid sequence shown in SEQ ID NO: 6. SEQ ID NO: 12 is where the sequence shown in SEQ ID NO: 25 is repeated 6 times in tandem and attached to the carboxy-terminus of the amino acid sequence shown in SEQ ID NO: 6. SEQ ID NO: 14 is where the sequence shown in SEQ ID NO: 25 is repeated 6 times in tandem and attached to the amino- and carboxy-termini of the amino acid sequence shown in SEQ ID NO: 6.

Furthermore, recombinant adhesive proteins containing the amino acid sequences shown in SEQ ID Nos: 10, 12, or 14 can additionally contain a peptide which has a purpose of facilitating purification. The peptide may be located on the amino- and/or the carboxy-termini of a recombinant adhesive protein, and examples of the peptide are GST and histidine tag. Recombinant adhesive proteins containing amino acid sequences as shown in SEQ ID Nos: 18, 20, or 22 are forms where a histidine tag is attached to the amino-terminus of a protein containing the amino acid sequences shown in SEQ ID Nos: 10, 12, or 14 respectively.

The adhesive protein of the present invention can further contain a peptide of 1 to 10 amino acids that are additionally inserted during cloning of the adhesive protein, at the amino-terminus, carboxy-terminus, or another kind of connective region of proteins.

The adhesive protein and recombinant adhesive protein of the present invention can be inserted into commonly used expression vectors constructed for expressing exogenous genes, and mass-produced through genetic engineering methods. The above vector may be selected according to the type and characteristics of the host cell used in the production of protein, or it may be newly constructed. Transforming the vector into the host cell and producing the recombinant protein from the transformant can easily be carried out through ordinarily employed methods. Selecting, constructing, transforming the vector and expressing the recombinant protein can be easily carried out by an ordinary person skilled in the art of the present invention, and partial variations in the ordinarily employed methods are also included in the present invention.

The sequence encoding an adhesive protein that is inserted into the vector is a sequence encoding an adhesive protein or a recombinant adhesive protein of the present invention, and is preferably selected from the group consisting of a nucleic acid encoding a protein that has at least 50% homology, preferably 80%, more preferably 90%, and most preferably at least 95% homology with the amino acid sequence shown in SEQ ID NOs: 6, 10, 12, or 14, a nucleic acid encoding a protein that has at least 50% homology, preferably 80%, more preferably 90%, and most preferably at least 95% homology with the amino acid sequence shown in SEQ ID NO: 6, 10, 12, or 14, where at least one sequence selected from the group consisting of SEQ ID NO:s 26 to 31 is tandemly repeated 1 to 10 times at the 5' and/or 3' ends of the nucleic acid, and the amino acid sequence shown in SEQ ID NO: 6, 10, 12, or 14, where 6 histidine residues are additionally attached at the amino-terminus. More preferably, a polynucleotide containing a sequence selected from the group consisting of SEQ ID NOs: 5, 7, 9, 11, 13, 15, 17, 19 and 21 can be inserted into the vector.

Figure 4:
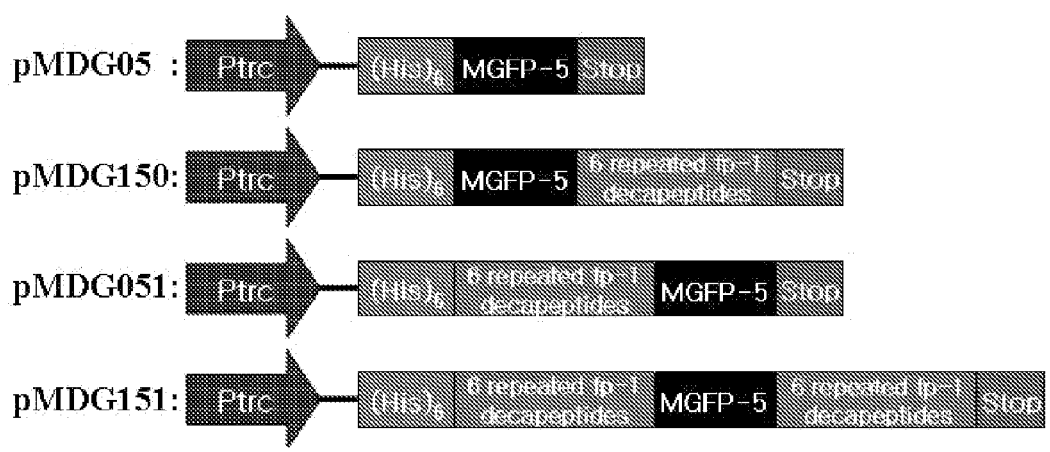
FIG. 4 shows vector diagrams of various combinations that can simultaneously express the 6×AKPSYPPTYK and the MGFP-5 gene.
Figure 7:
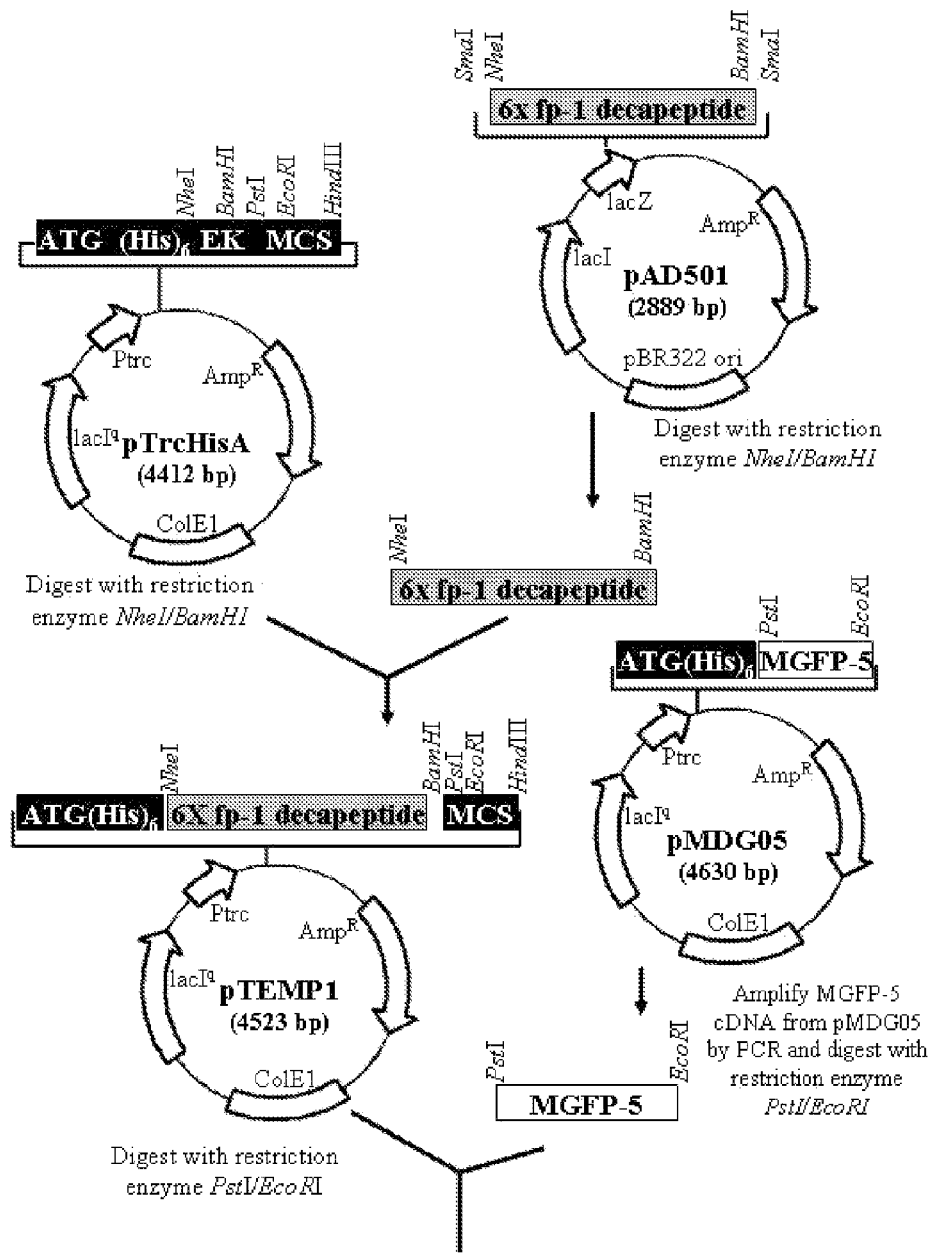
FIG. 7 is a diagram showing the procedure for constructing the pMDG151 vector for making the recombinant MGFP-151 nucleotide sequence.
Figure 7:
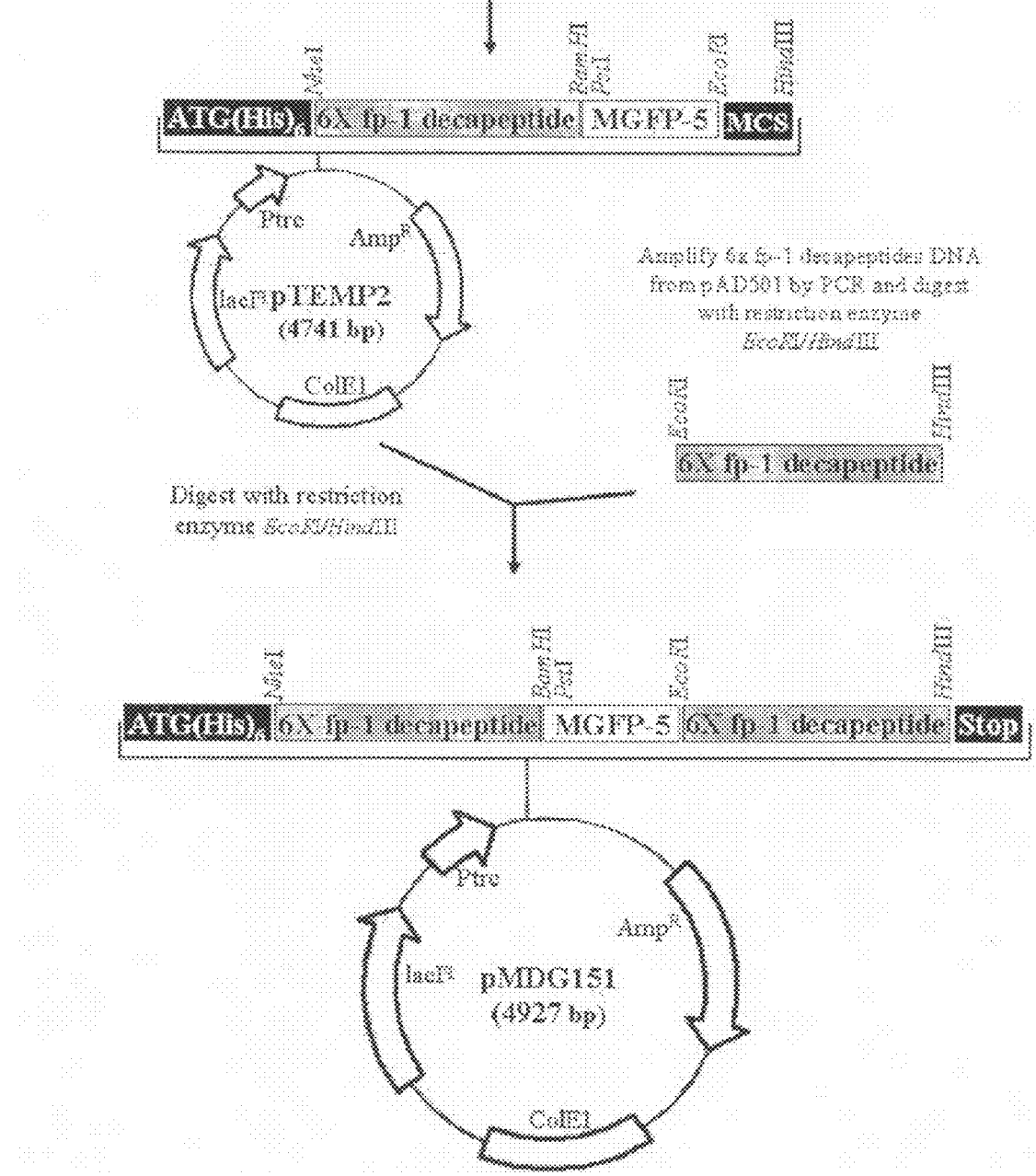
Figure 8:
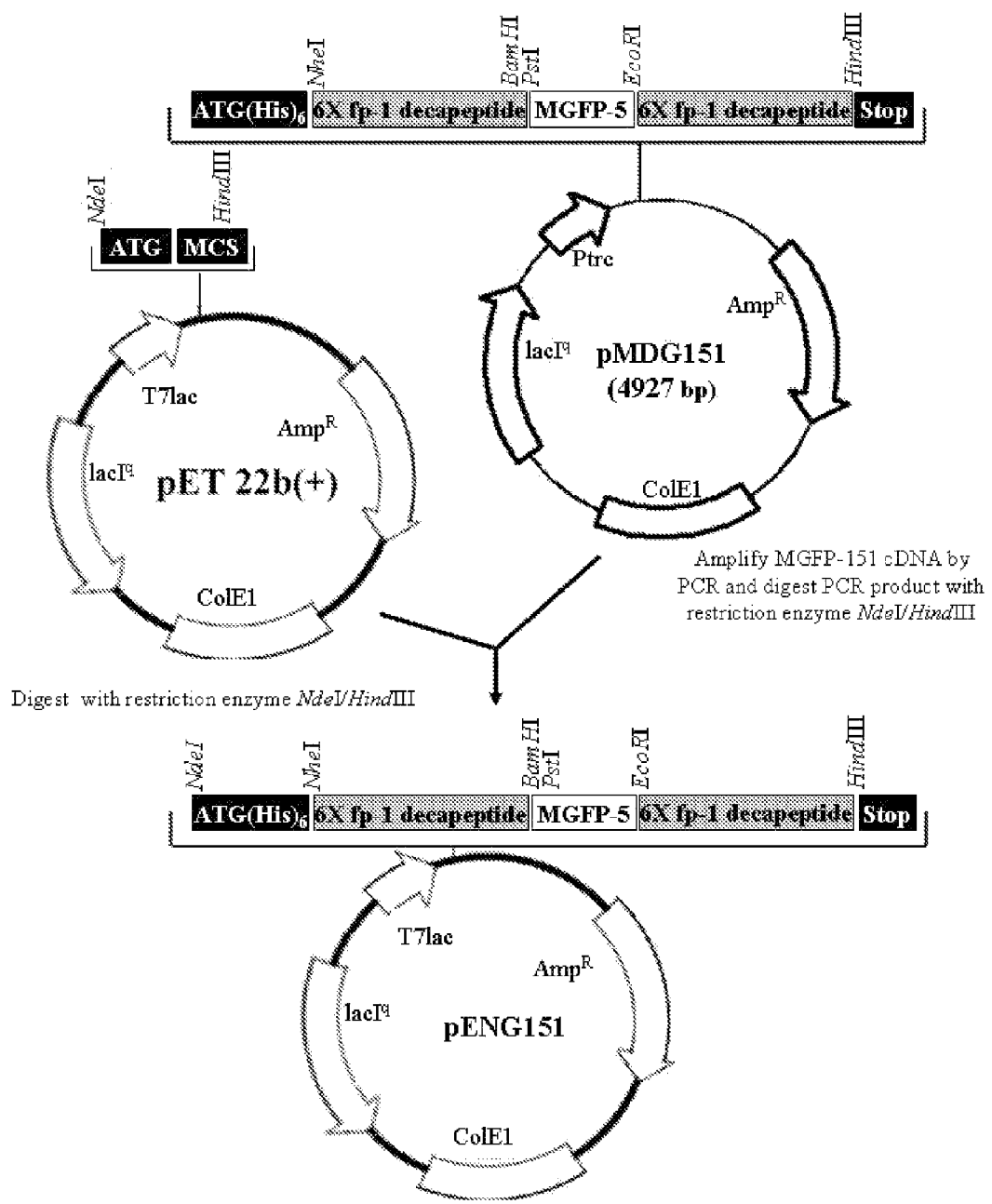
FIG. 8 is a diagram showing the procedure for constructing the pENG151 vector for making the recombinant MGFP-151 nucleotide sequence.
Figure 9:
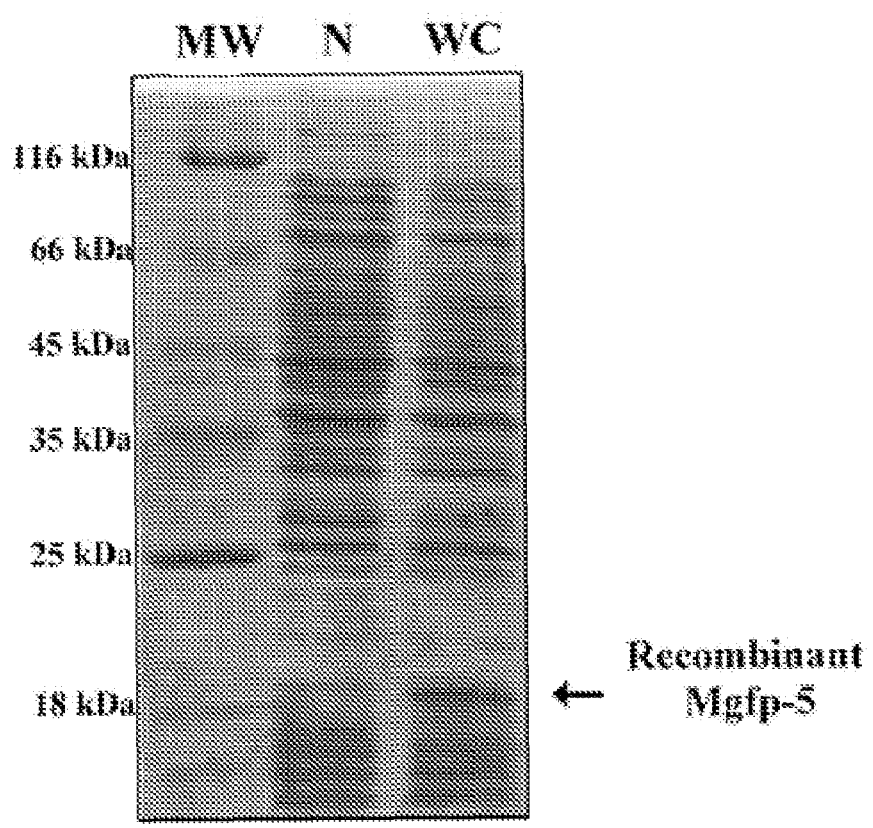
FIG. 9 is a photograph of the electrophoresis of each culture material of *E. coli* BL21/pMDG05 and *E. coli* BL21/pTrcHis (*E. coli* BL21/pTrcHisA transformed with pTrcHisA)

In an embodiment of the present invention, MGFP-5 sequence was cloned into a pGEM-T vector, and the sequence shown in SEQ ID NO: 7 (6×AKPSYPPTYK which is 6 tandem repeats of the amino acid sequence shown in SEQ ID NO: 25) was cloned into pUC18. Afterwards, the MGFP-5 sequence was cloned into a pTrcHisA vector to construct a pMDG05 vector (FIG. 4). Furthermore, in order to construct a vector that expresses a recombinant protein having a structure shown in Table 1 below, the sequences of MGFP-5 and SEQ ID NO: 7 were cloned into a pTrcHisA vector to construct pMDG150, pMDG051 and pMDG151 vectors (FIG. 7 to 9).

TABLE 1

| Hybrid adhesive protein | Structure (5' to 3') | Vector |
| --- | --- | --- |
| MGFP-15 | 6 × AKPSYPPTYK-MGFP-5 | pMDG150 |
| MGFP-51 | MGFP-5-6 × AKPSYPPTYK | pMDG051 |
| MGFP-151 | 6 × AKPSYPPTYK-MGFP-5-6 × AKPSYPPTYK | pMDG151 pENG151 |

The above pTrcHisA vector is a widely known vector which contains a trcpromoter, which allows expression of exogenous protein by induction using IPTG (isopropylthio-β-D-galactoside), and which has 6 histidine sequences for protein purification by affinity chromatography at the 5' end of the exogenous gene in order to facilitate protein purification. In the present invention, the pMDG05 vector was deposited at the Korean Collection for Type Cultures (KCTC) at the Biological Resource Center of Korea located at Eouen-dong, Yuseong-gu, Daejon, Republic of Korea as of Jun. 20, 2002, and received an accession number of KCTC 10291BP. The pENG151 vector was deposited as of Jan. 19, 2005 and given an accession number of KCTC 10766BP.

The expression vector for the adhesive protein and recombinant adhesive protein can be transformed into a host cell selected from the group consisting of prokaryotes, eukaryotes, and eukaryote-derived cells, in order to construct a transformant. The prokaryote is selected from the group consisting of *E. coli* and *Bacillus*, the eukaryote is selected from the group consisting of yeast, insects, animals, and plants, and the eukaryote-derived cells are plant cells, insect cells, and plants, but is not limited thereto.

As an embodiment, pMDG05, pMDG150, pMDG051 and pMDG151 vectors were each transformed into *E. coli* BL21, to construct *E. coli* BL21/pMDG05, *E. coli* BL21/pMDG150, *E. coli* BL21/pMDG051 and *E. coli* BL21/pMDG151. The aforementioned 4 types of transformants can be cultured in typical LB media, and IPTG can be added to induce protein expression. The preferred method of expression of recombinant protein is to culture in LB media (5 g/liter yeast extract, 10 g/liter Tryptone, 10 g/liter NaCl), and adding 0.1 to 10 mM of IPTG when the optical density of the culture solution is 0.6 to 0.9 at 600 nm, then culturing for 2 to 12 hours.

The recombinant protein expressed in the above method is expressed in a water-soluble and/or insoluble form within the transformant, so the isolation and purification depends on how it is expressed. When it is expressed in a water-soluble form, the recombinant protein can be purified by running the lysed cell supernatant through a chromatography column filled with an affinity resin such as a nickel resin. When it is expressed in a water-insoluble form, the recombinant protein can be purified by suspending the lysed cell pellet in an acidic organic solvent, preferably an organic solvent with a pH of 3 to 6, then centrifuging the suspension to isolate the upper layer. Examples of the acidic organic solvent are acetic acid, citric acid, and lactic acid, but is not limited thereto. The acetic acid used can be 5 to 30 (v/v) %, and preferably the cell pellet is dissolved in 20 to 30 (v/v) % acetic acid solution. The upper layer obtained through treatment with acidic organic solvent can further undergo gel filtration chromatography to further purify the recombinant protein.

Through the method of the present invention, 2-3 mg/L of the recombinant adhesive protein MGFP-5 of at least 95% purity can be obtained, and around 5 mg/L of MGFP-151 of at least 95% purity can be obtained. While MGFP-5 and MGFP-151 display similar levels of adhesion force, the solubility of MGFP-151 is significantly higher compared to MGFP-5, and thus MGFP-151 is easier to obtain in a concentrated form. In particular, MGFP-5 dissolves in a 5% acetic acid solution to a concentration of around 1 mg/mL, while MGFP-151 dissolves in water to a concentration of around 110 mg/mL, and dissolves in a 5% acetic acid solution to a concentration of around 220 mg/mL. The solubility of an adhesive protein is directly related to its ability to stay in highly concentrated forms, so the higher the solubility, the easier it is to make highly concentrated forms with high potential for industrial application. In this respect, it can be said that the adhesive protein MGFP-151 is more useful than MGFP-5.

The adhesive protein and the recombinant adhesive protein obtained through its expression in the present invention have adhesive activity and can be used as adhesives. The adhesive activity was confirmed through the experiment of modifying the tyrosine residues in the protein to 3,4-dihydroxyphenyl-L-alanine (DOPA). Thus, the adhesive protein of the present invention can not only be used as an adhesive for a wide variety of substrates, but also be used as a bioadhesive since it is harmless to the human body.

The present invention also provides an adhesive that contains adhesive protein as an active component. The adhesive protein can be a form where 5 to 100% of its tyrosine residues are modified to DOPA, and the adhesive can additionally contain a substance that modifies the tyrosine residues in the protein to DOPA. A typical example of the above substance is tyrosinase, but is not limited thereto.

The above adhesive can further contain 0.5 to 90% by weight of an excipient that is generally contained in bioadhesives or is pharmaceutically acceptable. Examples of excipients include surfactants, oxidants, and fillers, but are not limited thereto (see: US Pat. Application Publication No. 2003-65060 and U.S. Pat. No. 5,015,677). The surfactant can be cationic, anionic, non-ionic, or amphoteric, where examples are sodium dodecylsulfate and sodium dodecylbenzensulfonate. The oxidant can be selected from the group consisting of tyrosinase, catechol oxidase, glutaraldehyde, formaldehyde, bis(sulfosuccinimidyl)suberate, 3,3'-Dithiobis(sulfosuccinimidyl propionate), $O_2$, $Fe^{3+}$, $H_2O_2$ and $IO_4^-$ (see: *Macromolecules* 1998, 31, 4739-4745), and the filler can be selected from the group consisting of collagen, hyaluronic acid, condroitan sulfate, elastine, laminin, caseine, hydroxyapatite, albumin, fibronectin, and hybrin.

The adhesive of the present invention can be used to adhere or fix glass, plastic, polymer resin, or biological specimen, and the detailed mode and amount of usage, formulation and other such matters may follow Cell-Tak (BD Biosciences, Two Oak Park, Bedford, Mass., USA) which is currently available commercially. For example, the adhesive of the present invention can be a soluble, water-soluble, or insoluble formulation, and can be used in the amount of 0.01 to 100 $ug/cm^2$ for a substrate but is not limited thereto. Furthermore, the mode of use follows the general mode of adhesive use, and the typical mode is coating.

The aforementioned biological specimen refers to any animal or plant categorized as a biological organism and any part derived from such animal or plant. For example, it refers to cells, tissues, organs, RNA, DNA, protein, peptide, polynucleotide, hormones, and compounds, but is not limited thereto.

Examples of application of the adhesive of the present invention are as follows, but not limited thereto: (1) adhesion of substrates under water (fresh or salt water); (2) orthopedic treatments such as treatment of bone, ligament, tendon, meniscus, and muscle, and implant of artificial materials; (3) treatment of perforations, lacerations, and cuts, and ophthalmic attachments such as corneal implants and artificial corneal implants; (4) dental attachments such as holding retainers, bridges, or crowns in place, securing loose teeth, repairing broken teeth, and holding fillers in place; (5) surgical treatments such as attachment of blood vessels, attachment of cellular tissue, artificial material implants, and closure of wounds; (6) plant attachments such as bonding of transplanted parts and wound healing; (7) drugs, hormones, biological factors, medications, physiological or metabolic monitoring equipment, antibiotics, and cell transplant (see: U.S. Pat. No. 5,015,677).

The present invention also provides a method of adjusting the adhesion force of the above adhesive by treating with a substance selected from the group consisting of surfactant, oxidant, and filler, or controlling the concentration of the adhesive protein which is an active component of the adhesive (see: U.S. Pat. No. 5,015,677). The surfactant, oxidant, and filler are the same as was described above.

The present invention also provides a coating agent which contains the above adhesive protein as an active component. Since the adhesive protein of the present invention has the characteristic of adhering to glass, plastic, polymer resin, or biological specimen, it can not only be used as a coating agent for these substrates, but also coat the surface of substrates that are used underwater to prevent oxidation of the substrates, since the adhesive protein is water-resistant and water-repellent. An example of application of the coating agent is to coat the motor propeller of ships to prevent corrosion, but is not limited thereto. The above coating agent may consist solely of an adhesion protein, but can additionally contain commonly known adhesives, adhesive proteins other than the adhesive proteins of the present invention, resin contained in commonly known coating agents, organic solvents, surfactants, anticorrosive agents, or pigments. The content of the additional components may be appropriately adjusted within the commonly accepted range depending on the kind of component and formulation of the coating agent. Where an additional component is included, the adhesive protein as an active component is contained in the coating agent at a level that maintains the adhesive activity, and can for example be contained in the coating agent at 0.1 to 80% by weight.

The coating agent of the present invention can be manufactured in the form of cream, aerosol (spray), solid, liquid, or emulsion, but is not limited to these formulations.

Embodiments of the present invention are described below. The following embodiments are merely illustrative of the present invention and the present invention is not limited to the following embodiments.

In the following, the mussel used for cloning the MGFP-5 gene was *Mytilus galloprovincialis*.

EXAMPLE 1

Cloning of the MGFP-5 Gene

In order to clone MGFP-5, the primer shown in SEQ ID NO: 1 (5'-ggcctgcagcagttctgaagaatacaaggg-3) and the primer shown in SEQ ID NO: 2 (gtagatctatacgccggaccagtgaacag) were each synthesized. PCR was run 30 times using the mussel cDNA library, and a PCR product of 243 bp was obtained (FIG. 1). The above PCR product was cloned in a pGEM-T vector (Promega).

To obtain the upstream signal sequence of MGFP-5, nested PCR was executed using mussel (*M. galloprovincialis*) cDNA library. The primers used were a T3 promoter primer of the ZAP vector (SEQ ID NO: 32) and the primer shown in SEQ ID NO: 3 (5'-cttgtattttccgctgttttt-3'). An amplification product of around 300 bp was obtained through the PCR and it was cloned into a pGEM-T vector.

To obtain the C-terminal poly-A tail region of MGFP-5, nested PCR was performed using SEQ ID NO: 4 (5'-aaaaa-cagcggaaaatacaag-3') and T7 promoter primer (SEQ ID NO: 33). The amplification product of 350 bp was obtained and cloned into a pGEM-T vector.

The MGFP-5 cDNA nucleotide sequence obtained from the above was analyzed, and the MGFP-5 nucleotide sequence excluding the secretion signal sequence is shown in SEQ ID NO: 5, and the amino acid sequence encoded therein is shown in SEQ ID NO: 6.

EXAMPLE 2

Construction of the Vector for Genetically Engineered Production of MGFP-5

The MGFP-5 cDNA in the pGEM-T vector was isolated by using the restriction enzyme sites PstI and EcoRI, then inserted into a pTrcHis A vector (Invitrogen, USA) that was cleaved with PstI and EcoRI restriction enzymes to construct pMDG05 (4630 bp). The pMDG05 vector was deposited at the Korean Collection for Type Cultures (KCTC) at the Biological Resource Center of Korea located at Eoeun-dong, Yuseong-gu, Daejon, Republic of Korea as of Jun. 20, 2002, and received a accession number of KCTC 10291 BP.

The pMDG05 vector contains a trc promoter for expression in *E. coli*, and allows induction of expression using IPTG (Sigma, USA). It also has 6 histidine residues at the 5' end of the MGFP-5 gene for protein isolation and purification by affinity chromatography.

EXAMPLE 3

Construction of the Peptide (6×AKPSYPPTYK) Derived from FP-1

From the amino acid sequence of FP-1 (Genbank No. Q27409 or S23760), an FP-1 derivative as shown in SEQ ID NO: 25 where the peptide "AKPSYPPTYK" is tandemly repeated 6 times (referred to as "6×AKPSYPPTYK") was constructed.

Figure 3:
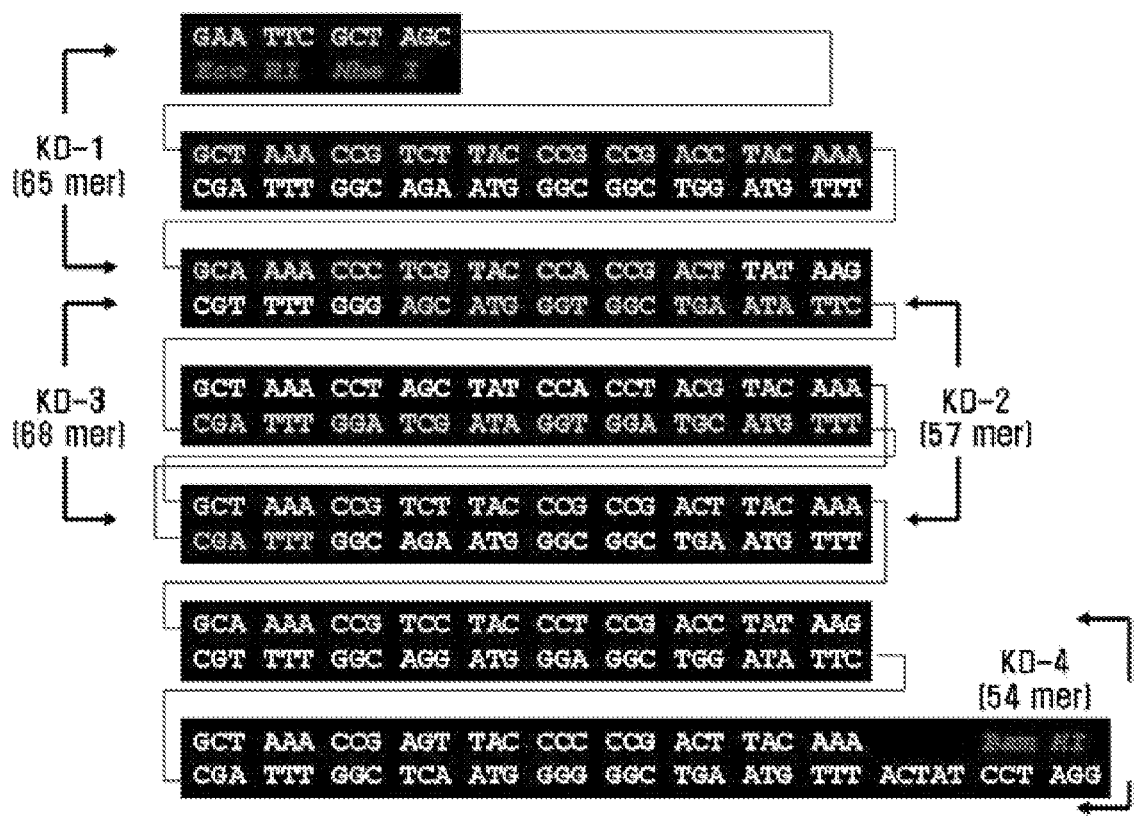
FIG. 3 shows the FP-1 variant (referred to as "6×AKPSYPPTYK" from hereon) where the peptide AKPSYPPTYK is tandemly attached 6 times, and the 4 oligomers KD-1, KD-2, KD-3, and KD-4 that were used in its synthesis.

That is, KD-1 to KD-4 described in FIG. 3 was each synthesized, and then annealed, to synthesize 6×AKPSYPPTYK in SEQ ID NO: 8 encoding the FP-1 variant in SEQ ID NO: 7. Additionally, at the 5' end of the 6×AKPSYPPTYK, EdoRI and NheI restriction enzyme sites in the direction of 5' to 3' were placed, and a BamHI restriction enzyme site was placed at the 3' end (FIG. 3). The 6×AKPSYPPTYK was inserted into a pUC18 vector using the NheI and BamHI restriction enzyme sites to construct the pAD501 vector (M. Kitamura, 1999, Journal of Polymer Science Part A: Polymer Chemistry 37, 729-736).

In FIG. 3, the "ACTAT" located at the 5' side of the BamHI site in the polynucleotide was inserted to preserve the ORF.

EXAMPLE 4

Construction of Recombinant Hybrids of FP-1 and MGFP-5

From hereon, MGFP-5 is referred to as "MGFP-5", a hybrid where 6×AKPSYPPTYK of Example 3 is attached to the N-terminus of MGFP-5 is referred to as "MGFP-15", a hybrid where 6×AKPSYPPTYK is attached to the C-terminus of MGFP-5 is referred to as "MGFP-51", and a hybrid where 6×AKPSYPPTYK is attached to both the N- and C-termini of MGFP-5 is referred to as "MGFP-151" (see Table 1 above).

The hybrids MGFP-15 shown in SEQ ID NO: 10, MGFP-51 shown in SEQ ID NO: 12, and MGFP-151 shown in SEQ ID NO: 14 were constructed, and they include histidine tags (6×His) and other amino acid residues at the 5' end and amino acid residues between the 6×AKPSYPPTYK and MGFP-5 due to the design of the experiment.

In order to express each of the hybrids MGFP-5, MGFP-15, MGFP-51 and MGFP-151, the structures shown in SEQ ID Nos: 15, 17, 19, and 21 were inserted into a vector to respectively construct pMDG05, pMDG150, pMDG051, and pMDG151 of FIG. 4. In the above 4 vectors, expression is controlled by a trc promoter that is inducible by IPTG (Sigma, US), and there are 6 histidine residues at the 5' region and a translation termination codon (TAA) at the 3' end of each recombinant construct.

The method of construction for each vector is as follows.

Figure 5:
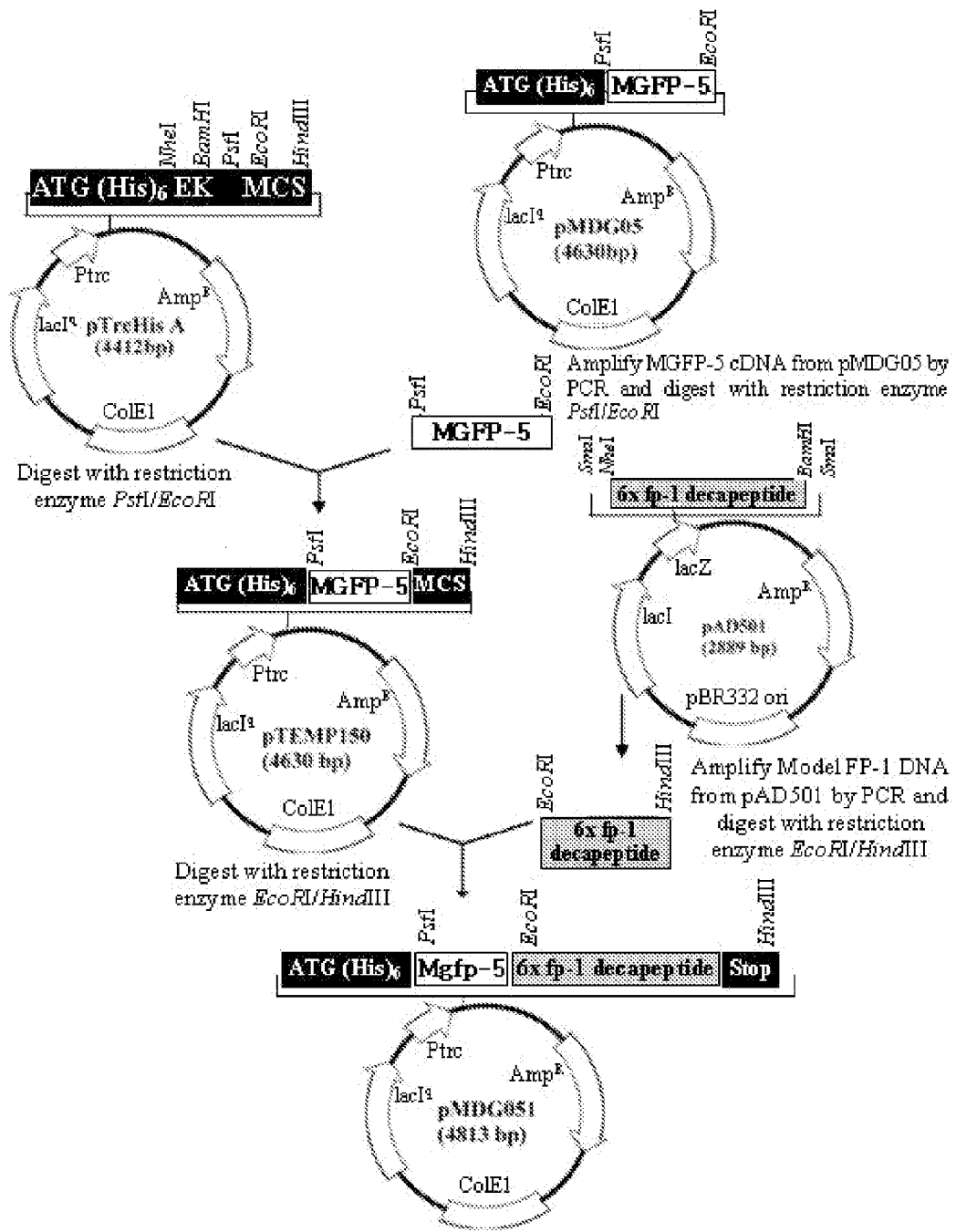
FIG. 5 is a diagram showing the procedure for constructing the pMDG051 vector for making the recombinant MGFP-51 nucleotide sequence.

PCR was executed on the nucleotide sequence of MGFP-5 within the pMDG05 vector of Example 2 with the primer set shown in SEQ ID NOs: 1 and 2, then cleaved with PstI and EcoRI restriction enzymes, then inserted into a pTrcHis A vector (Invitrogen, USA) which was previously cleaved with the same enzymes, to construct pTEMP150 (4630 bp). Also, the 6×AKPSYPPTYK in the pAD501 vector of Example 2 was amplified with the primer set shown in SEQ ID NO: 23 (5'-GGT ACC CGA ATT CGAATTCGC TAA ACC G-3') and 24 (5'-GGT CGA CTC AAGCTT ATC ATT TGT AAG TCG-3'), and cleaved with EcoRI and Hind III restriction enzymes. Then it was inserted into pTEMP150 which was previously cleaved with EcoRI and Hind III, to construct pMDG051 (FIG. 5).

Figure 6:
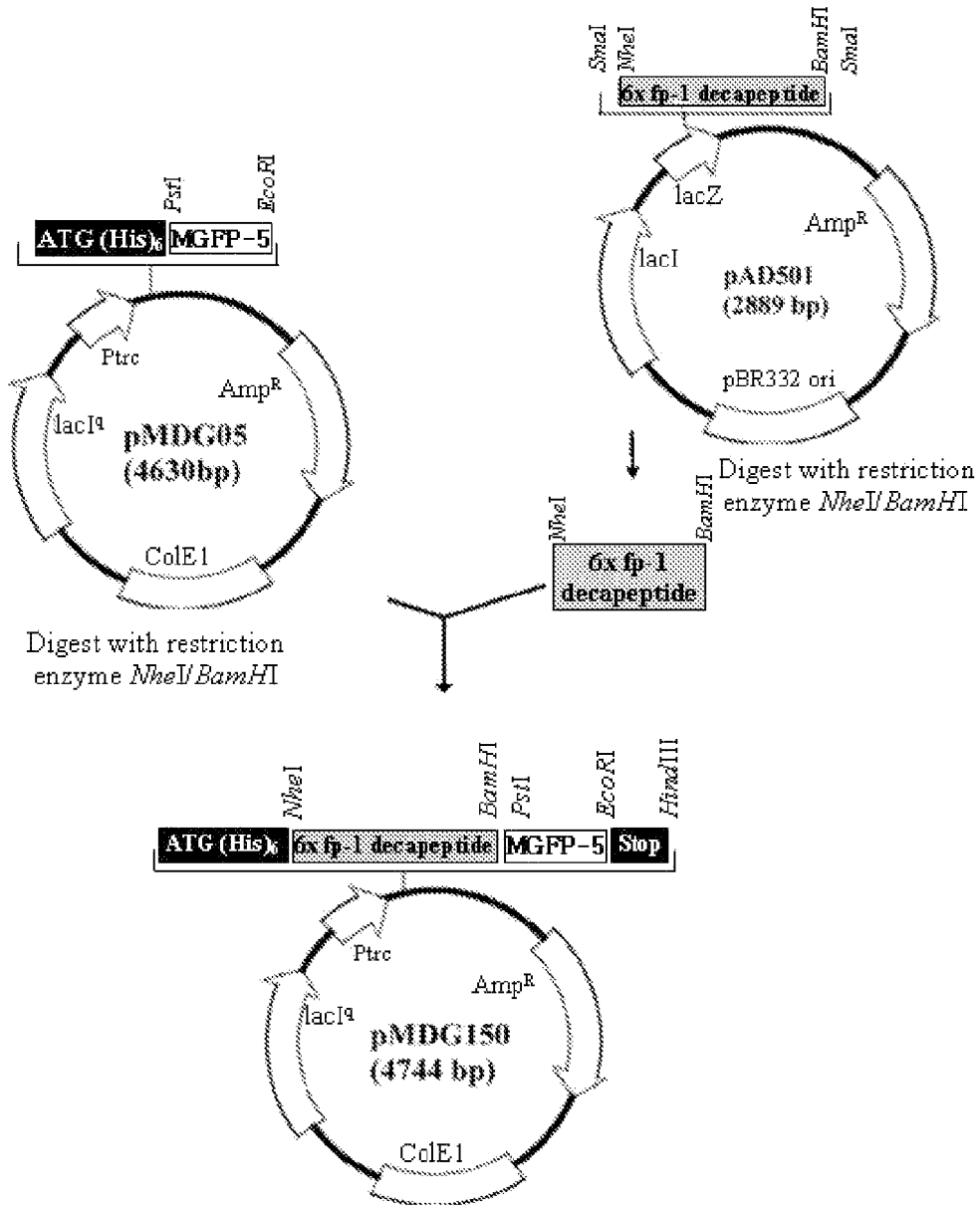
FIG. 6 is a diagram showing the procedure for constructing the pMDG150 vector for making the recombinant MGFP-15 nucleotide sequence.

The 6×AKPSYPPTYK in the pAD501 vector was isolated by treating with Nhe I and BamH I restriction enzymes, and inserted into a pMDG05 vector which was treated with the same enzymes to construct pMDG150 (FIG. 6).

The 6×AKPSYPPTYK in the pAD501 vector was isolated by treating with Nhe I and BamH I restriction enzymes, and inserted into a pTrcHis A vector (Invitrogen, USA) which was treated with the same enzymes, to construct pTEMP1 (4523 bp). Then the nucleotide sequence of MGFP-5 within the pMDG05 vector was amplified with the primer set shown in SEQ ID NOs: 1 and 2, then cleaved with PstI and EcoRI restriction enzymes, then inserted into pTEMP1 which was treated with the same enzymes, to construct pTEMP2 (4741 bp). Also, the 6×AKPSYPPTYK in the pAD501 vector was amplified with the primer set shown in SEQ ID NOs: 23 and 24, then cleaved with EcoRI and Hind III restriction enzymes. Then it was inserted into pTEMP2 which was cleaved with EcoRI and Hind III, to construct pMDG151 (4927 bp) (FIG. 7).

Also, in order to express the MGFP-151 nucleotide at a high level, the MGFP-151 nucleotide was amplified from the pMDG151 vector with the primers shown in SEQ ID NO: 34 (5'-CCT AACATATGG GGG TTC TCA TCA TC-3') and SEQ ID NO: 35 (5'-ATC CGC CAA AAC AGC C AAGCTT-3'). The amplified product was inserted into a pET 22b(+) vector (Novagen, EMB Bioscience, Inc. 441 Charmany Dr. Madison, Wis. 53719 USA) using Nde I and Hind III restriction enzymes, to construct a pENG151 vector (FIG. 8). The pENG151 vector was transformed into *E. coli*, and deposited at the Korean Collection for Type Cultures (KCTC) at the Biological Resource Center of Korea as of Jan. 19, 2005 and given an accessiont number of KCTC 10766BP.

EXAMPLE 5

Construction of Transformant Producing MGFP-5 and Hybrids

Competent cells of *E. coli* Top 10 (F-mcrA(mrr-hsdRMS-mcrBC)Φ801acZΔM15 ΔlacX74 deoR recA1 araD139 Δ(ara-leu)7697 galU galK rpsL (Strr) endA1 nup, Invitrogen) used for cloning, and *E. coli* BL21 (F-ompT hsdSB (rB-mB-) gal dc) used for protein expression were each prepared using $CaCl_2$ buffer. Transformation of each of the pMDG05, pMDG051, pMDG150 and pMDG151 vectors in Example 4 into the competent cells were achieved by a heat shock method (leaving for 2 minutes at 42° C.). Then through a selection process using ampicillin (Sigma) the transformants *E. coli* Top10/pMDG05, *E. coli* Top10/pMDG051, *E. coli* Top10/pMDG150, *E. coli* Top10/pMDG151, *E. coli* BL21/pMDG05, *E. coli* BL21/pMDG051, *E. coli* BL21/pMDG150 and *E. coli* BL21/pMDG151 were each obtained.

EXAMPLE 6

Expression and Purification of MGFP-5 from *E. coli* BL21/pMDG05

6-1. Culture of *E. coli* BL21/pMDG05
*E. coli* BL21/pMDG05 was cultured in LB media (5 g/liter yeast extract, 10 g/liter Tryptone and 10 g/liter NaCl), and IPTG was added to a final concentration of 1 mM when the optical density of the culture solution was 0.7 to 0.8 at 600 nm, to induce expression of recombinant adhesive protein MGFP-5. At this time, a culture solution in 10 mL of LB media (with 500 µg of added ampicillin) cultured for 12 hours in a sterile 50 mL tube was inoculated into 100 mL of LB media contained in a 500 mL flask. The *E. coli* BL21/pMDG05 culture was centrifuged at 18,000 g for 4 to 10 minutes to obtain the cell pellet, and this was stored at −80° C.

6-2. Confirmation of MGFP-5 Expression
The cell pellet was resuspended in SDS-PAGE buffer (0.5 M Tris-HCl, pH 6.8, 10% glycerol, 5% SDS, 5% β-mercaptoethanol, 0.25% bromophenol blue) 100 µl, and denatured by boiling at 100° C. for 5 minutes. For SDS-PAGE analysis, the samples were electrophoresed on a 15% SDS-polyacylamide gel and then the protein bands detected using Coomassie blue staining (Bio-Rad) or silver staining (Bio-Rad, USA). For Western blot analysis, the samples were electrophoresed on a 15% SDS-polyacylamide gel and then transferred onto a nitrocellulose membrane at 15 V. The MGFP-5 protein transferred onto the nitrocellulose membrane was detected using a monoclonal anti-histidine ligand antibody (R&D Systems, USA) and a colorimetric reaction.

FIG. 9 is an electrophoretic image of the culture product of *E. coli* BL21/pMDG05 and *E. coli* BL21/pTrcHis (*E. coli* BL21/pTrcHisA transformed with pTrcHisA), where MW is a size marker, N is a control group, and WC is the culture product of *E. coli* BL21/pMDG05. FIG. 9 confirmed the expression of MGFP-5 protein in *E. coli* BL21/pMDG05.

To confirm the expressed form of recombinant MGFP-5 in the cell sample, SDS-PAGE and Western blot was carried out on each of the cell debris and soluble supernatant obtained from lysis of the cell pellet, and the cell pellet.

That is, *E. coli* BL21/pMDG05 cell pellets were resuspended in 5 ml Buffer B (8M urea, 10 mM Tris-Cl, 100 mM sodium phosphate, pH 8.0) per 1 gram cells, and were lysed by gentle shaking for 1 h at room temperature. The lysate was centrifuged at 14,000 rpm for 20 min to obtain the soluble supernatant and insoluble cell debris.

Figure 10:
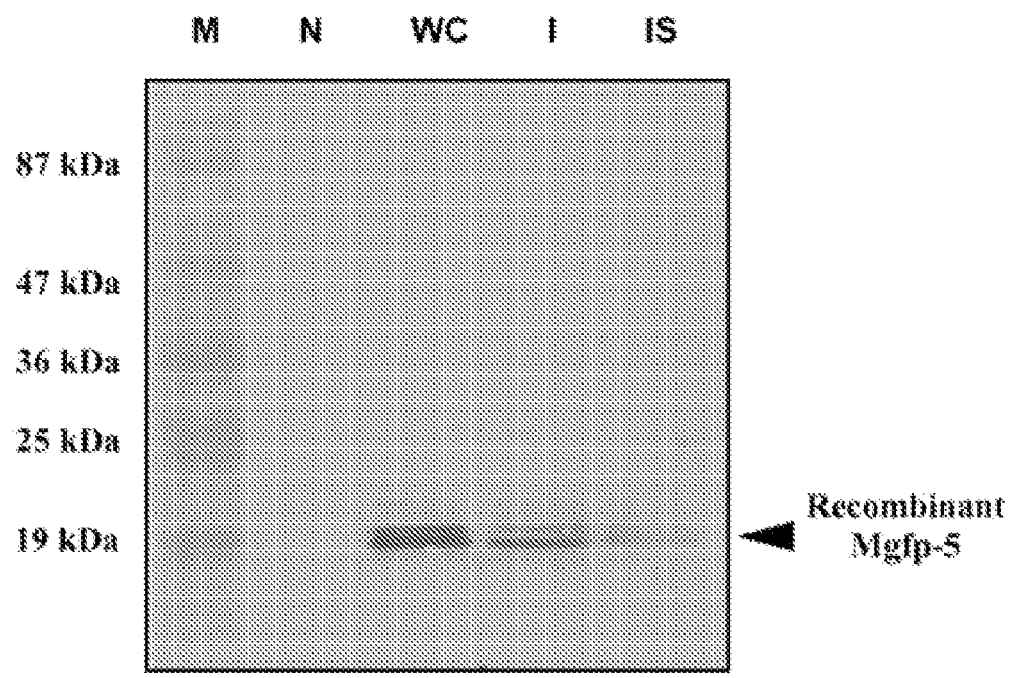
FIG. 10 is a Western blot photograph of an SDS-PAGE of the whole cell pellet (WC), soluble upper fraction (I), and insoluble cell debris fraction (IS) isolated from *E. coli* BL21/pMDG05 culture solution, and negative control (N).

FIG. 10 is a Western blot image of the SDS-PAGE analysis of the cell pellet (WC), soluble supernatant (I), the insoluble cell debris (IS) isolated from the culture solution of *E. coli* BL21/pMDG05 and the negative control (N). FIG. 10 shows that the MGFP-5 protein is detected at high levels in the soluble supernatant fraction, indicating that it is expressed in a soluble form inside the cell.

6-3. Purification of Recombinant MGFP-5 Protein
In order to isolate and purify recombinant MGFP-5 which is expressed in a soluble form within *E. coli* BL21/pMDG05, affinity chromatography utilizing the histidine affinity ligand contained in the pMDG05 vector was carried out.

Immobilized metal affinity chromatography (IMAC) purification was performed using the Acta Prime Purification System (Amersham Biosciences) at room temperature at a 1 ml per min flow rate. 10 ml Ni—NTA™ Agarose (Qiagen) charged with 0.1 M $NiSO_4$ (Samchun Chemicals) was used as the resin, and separation was performed under denaturing conditions. After the column was filled with the resin, it was equilibrated with buffer (8M urea, 10 mM Tris-Cl, 100 mM sodium phosphate, pH 8.0). Then the soluble supernatant fraction was loaded onto the column, and then the column was eluted with Buffer A (8M urea, 10 mM Tris-Cl, 100 mM sodium phosphate, pH 6.3) and Buffer B (8M urea, 10 mM Tris-Cl, 100 mM sodium phosphate, pH 5.9). Recombinant MGFP-5 protein was eluted with elution buffer (8M urea, 10 mM Tris-Cl, 100 mM sodium phosphate, pH 4.5), and eluted fractions were all collected and dialyzed in 5% acetic acid at 4° C. (Spectra/Por® molecular porous membrane tubing, Spectrum Laboratories, USA).

Figure 11:
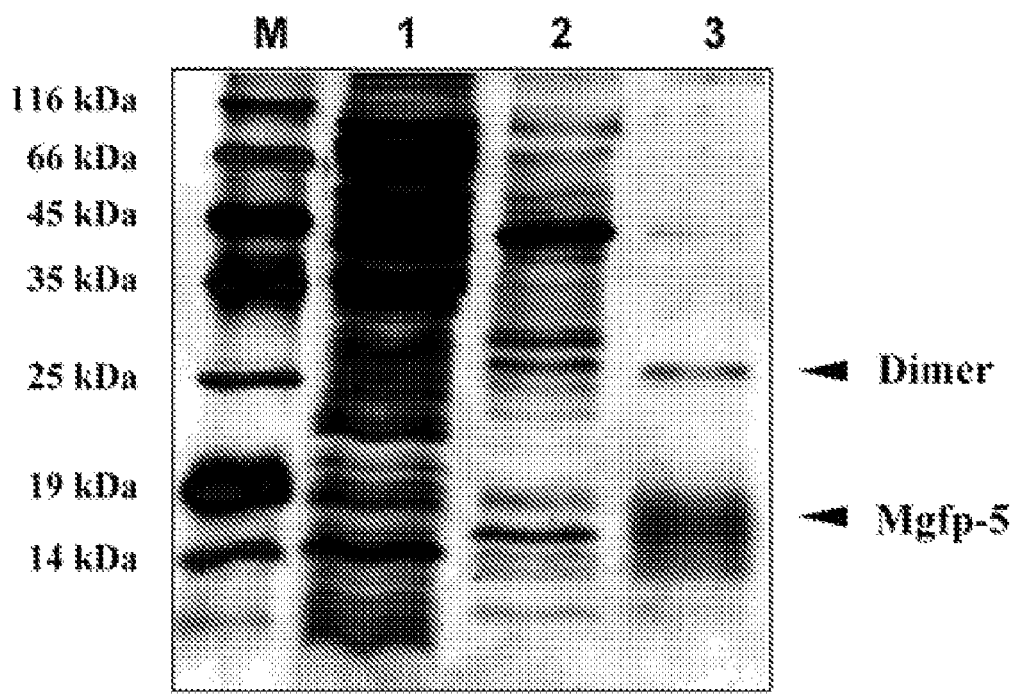
FIG. 11 is a photograph of silver-stained SDS-PAGE of affinity chromatography fractions for purification of recombinant MGFP-5 protein from *E. coli* BL21/pMDG05.

FIG. 11 is an image of silver-stained SDS-PAGE of affinity chromatography fraction samples during the purification of recombinant MGFP-5 protein from *E. coli* BL21/pMDG05. M is a size marker, Lane 1 is the fraction that was adsorbed when the soluble supernatant fraction was loaded onto the column, Lane 2 is the eluted fraction obtained at the step of washing the column, and Lane 3 is the eluted fraction separated by the elution buffer. FIG. 11 shows that the recombinant is purified at a high level of purity.

6-4. Analysis of MGFP-5 Recombinant Protein
MALDI-TOF (Matrix-assisted laser desorption ionization with time-of-flight) mass spectrometry analysis was performed using a PerSeptive Voyager DE instrument (Perkin-Elmer).

Sinapinic acid in 30% acetonitrile and 0.1% trifluoroacetic acid was used as matrix solution. The recombinant MGFP-5 protein obtained from the above section 6-3 was diluted 1:25 with the matrix solution, then 1 µl was spotted onto gold plates and evaporated using a vacuum pump. Mass spectra were acquired in positive ion mode using an accelerating voltage of 25,000 V, grid voltage at 70 to 80%, guide wire voltage at 0.3%, delay time of 200 to 500 ns and $N_2$ laser power at 1600 to 1900 (arbitrary units). Internal calibration was performed using BSA with $[M+H]^+$ at 66.431 and $[M+2H]^{2+}$ at 33.216.

Figure 12:
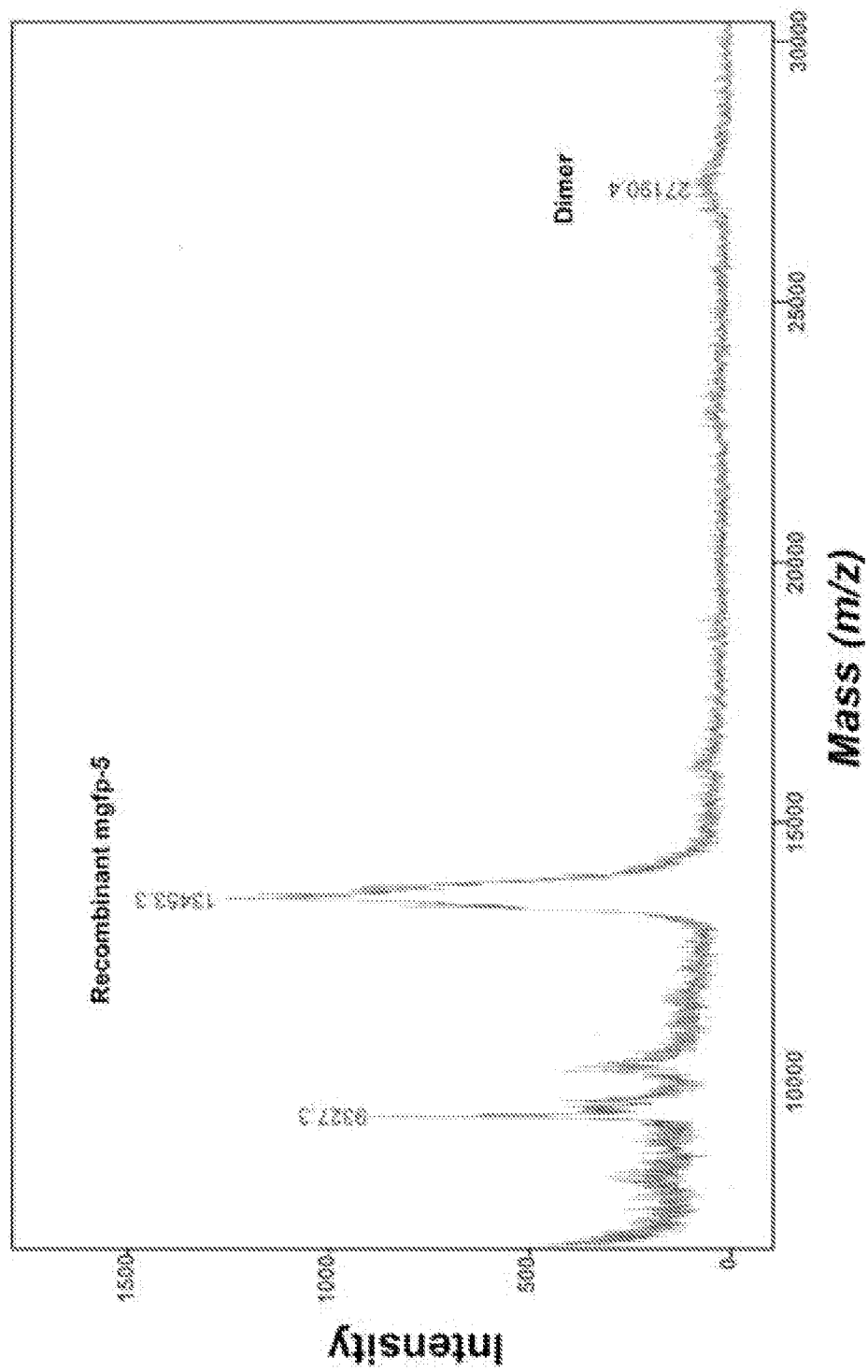
FIG. 12 is a mass spectrometry result of purified recombinant MGFP-5 protein.

FIG. 12 is the result of mass spectrometry analysis of MGFP-5 recombinant protein.

EXAMPLE 7

Expression and Purification of MGFP-51 from E. coli BL21/pMDG051

E. coli BL21/pMDG051 was cultured and the cell pellet, cell debris and soluble supernatant fractions were each obtained in the same method as in Example 6. Afterwards, SDS-PAGE and Western blot was carried out on each of the above samples.

Figure 13:
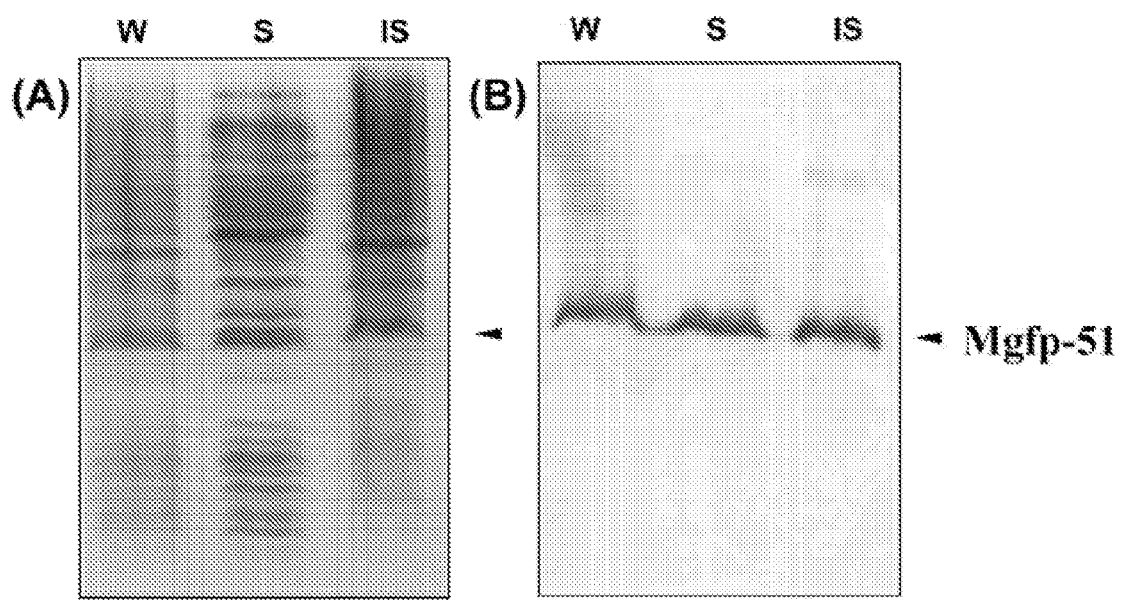
FIG. 13 shows (A) Coomassie blue-stained SDS-PAGE and (B) Western blot analyses of recombinant MGFP-51 protein from *E. coli* BL21/pMDG051.

FIG. 13 shows photographs of SDS-PAGE analysis (A) and a Western blot analysis (B) of the expression of recombinant MGFP-51 protein from E. coli BL21/pMDG051. W is cell pellet, S is soluble supernatant fraction, and IS is insoluble cell debris. FIG. 13 shows that the recombinant MGFP-5 protein is expressed within the cell in both soluble and insoluble forms.

EXAMPLE 8

Expression and Purification of MGFP-15 from E. coli BL21/pMDG150

E. coli BL21/pMDG150 was cultured and the cell pellet, cell debris and soluble supernatant fractions were each obtained in the same method as in Example 6. Afterwards, SDS-PAGE and Western blot was carried out on each of the above samples.

Figure 14:
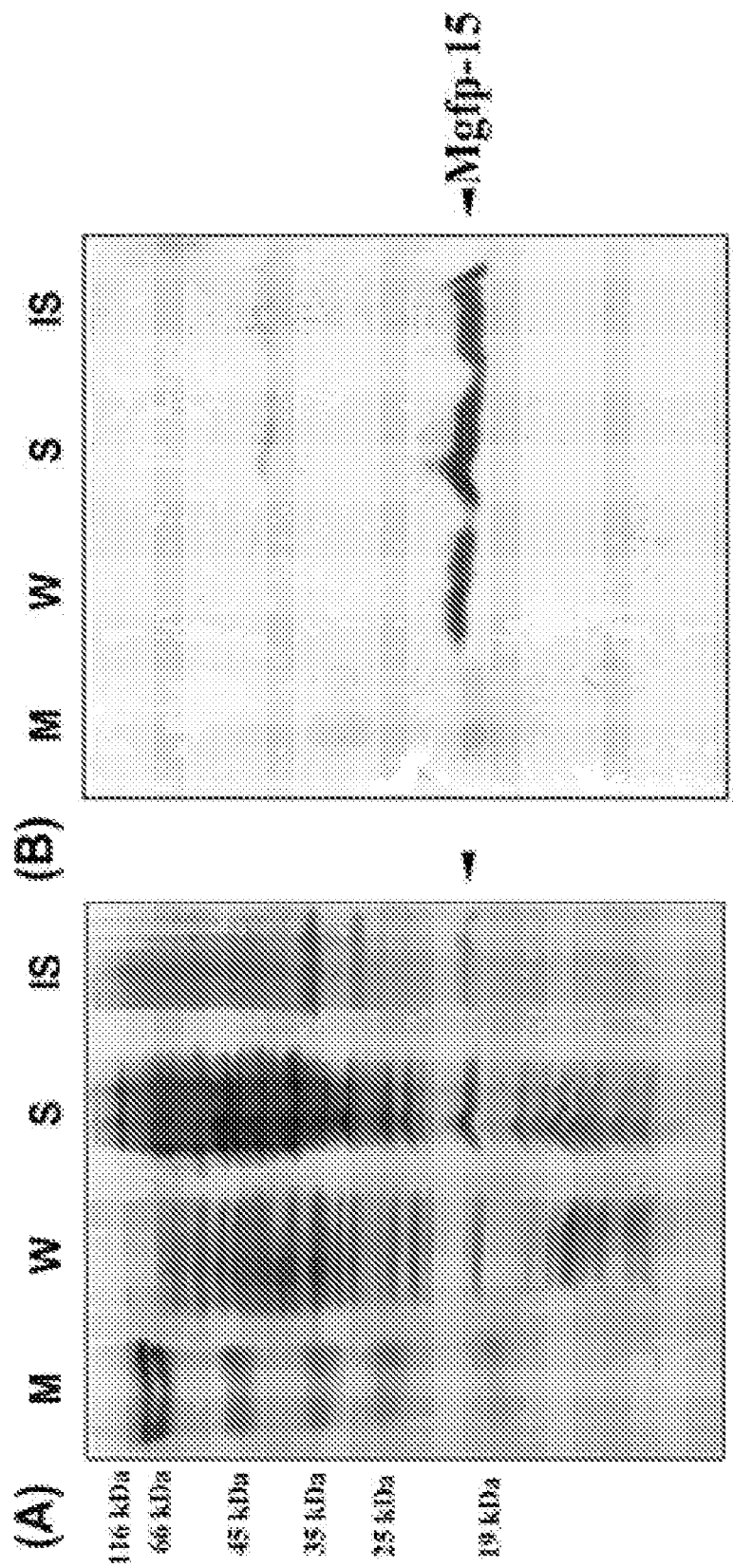
FIG. 14 shows (A) SDS-PAGE and (B) Western blot analyses of recombinant MGFP-15 protein from *E. coli* BL21/pMDG150.

FIG. 14 shows photographs of SDS-PAGE analysis (A) and a Western blot analysis (B) of the expression of recombinant MGFP-15 protein from E. coli BL21/pMDG150. M is a size marker, W is cell pellet, S is soluble supernatant fraction, and IS is insoluble cell debris. FIG. 14 shows that the recombinant MGFP-15 protein is expressed within the cell in both soluble and insoluble forms.

EXAMPLE 9

Expression and Purification of MGFP-151 from E. coli BL21/pMDG151

9-1. Expression of MGFP-151

E. coli BL21/pMDG151 was cultured and the cell pellet, cell debris and soluble supernatant fractions were each obtained in the same method as in Example 6. Afterwards, SDS-PAGE and Western blot was carried out on each of the above samples.

Figure 15:
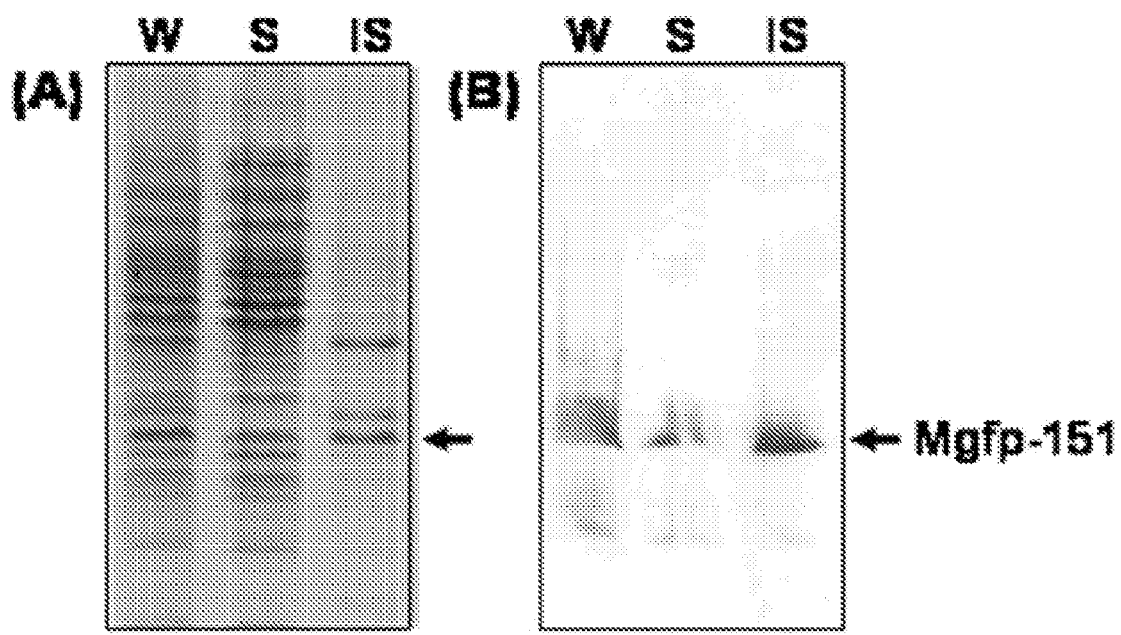
FIG. 15 shows (A) SDS-PAGE and (B) Western blot analyses of recombinant MGFP-151 protein from *E. coli* BL21/pMDG151.

FIG. 15 shows photographs of SDS-PAGE analysis (A) and a Western blot analysis (B) of the expression of MGFP-151 recombinant protein from E. coli BL21/pMDG151. W is cell pellet, S is soluble supernatant fraction, and IS is insoluble cell debris. FIG. 15 shows that the MGFP-151 recombinant protein is expressed within the cell in soluble and insoluble forms.

9-2. Purification I of Recombinant MGFP-151 Protein

Cell pellets were resuspended in 5 ml lysis buffer (10 mM Tris-Cl, 100 mM sodium phosphate, pH 8.0) per gram of cell pellet, then the cells were lysed at 20,000 PSI (Constant systems, Low March, UK). Cell lysates were centrifuged at 18,000 g and 4° C. for 20 min to collect the cell debris. The cell debris was resuspended in 20 ml of 5, 10, 15, 20, 25, 30, 22, 24, 26 and 28 (v/v) % acetic acid solutions per gram cell weight respectively and centrifuged under the same conditions. The supernatant was prepared into a chromatographic sample.

Figure 16:
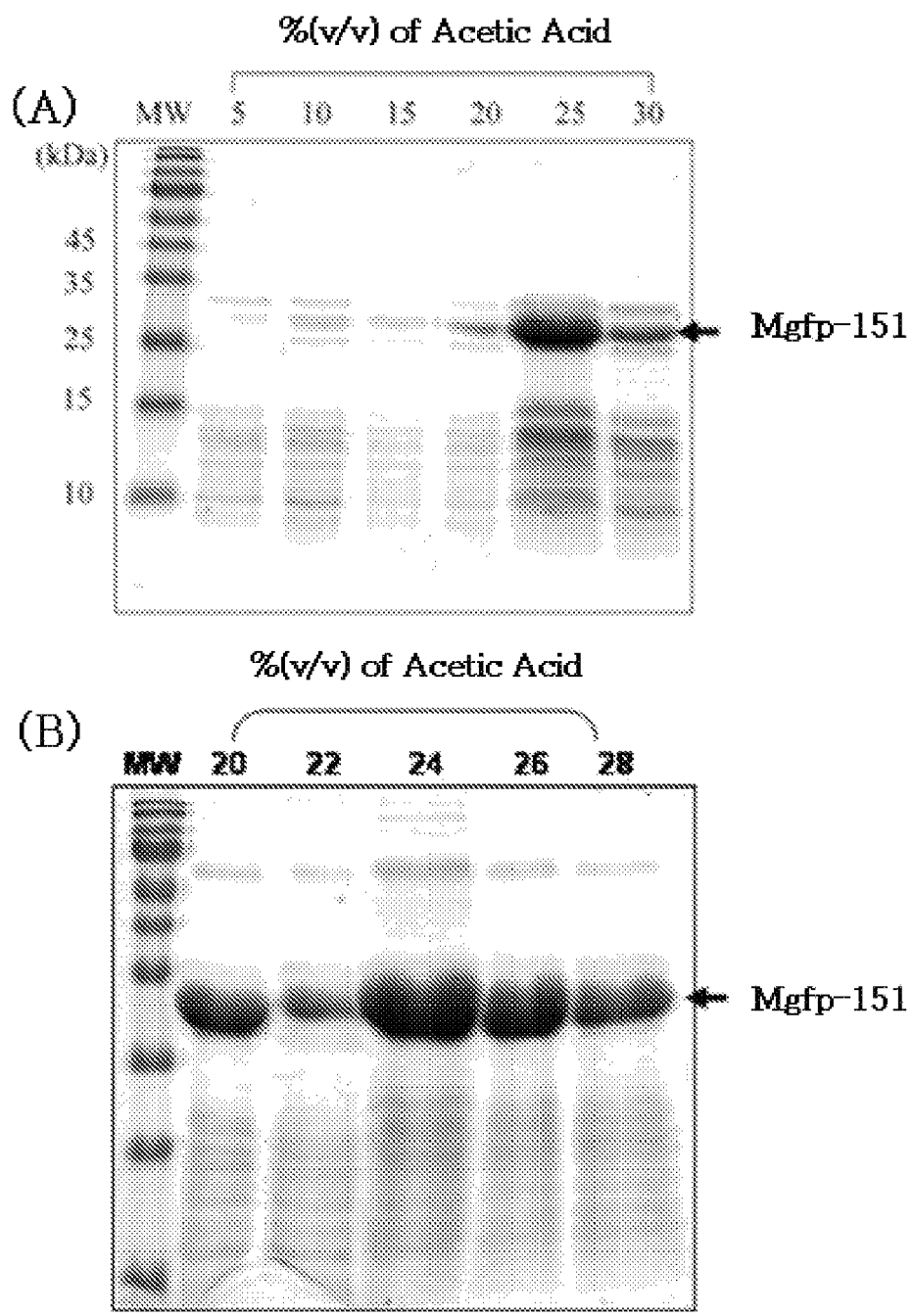
FIG. 16 shows the recovery rates of recombinant MGFP-151 protein expressed from *E. coli* BL21/pMDG151 according to the concentration of acetic acid solution.

A 40 cm×2.6 cm column was filled with Sephacryl S-300 HR (Pharmacia), and equilibrated with 5% acetic acid. Afterwards, 2 ml of sample was loaded, and then the sample was eluted with the concentrations of acetic acid that were used to resuspend each sample to collect the eluted fractions. The degree of purification of MGFP-151 in each concentration of acetic acid elution fraction was confirmed by SDS-polyacylamide gel electrophoresis and then staining by Coomassie blue (FIG. 16). FIG. 16 shows that recombinant MGFP-151 protein is eluted at an acetic acid concentration of 20 to 30 (v/v) %. In particular, it was confirmed that dilution in 25% acetic acid solution showed the best results with 74% purity and 45% yield.

9-3. Purification II of Recombinant MGFP-151 Protein

Cell pellets were resuspended in 5 ml lysis buffer (10 mM Tris-Cl, 100 mM sodium phosphate, pH 8.0) per gram of cell pellet, then the cells were lysed at 20,000 PSI (Constant systems, Low March, UK). Cell lysates were centrifuged at 18,000 g and 4° C. for 20 min to collect the cell debris. The cell debris was resuspended in 20 ml of 25% acetic acid solution per gram cell weight, and centrifuged under the same conditions. After the supernatant was freeze-dried, it was dissolved in 2 ml of 5% acetic acid and prepared into a chromatographic sample.

Figure 17:
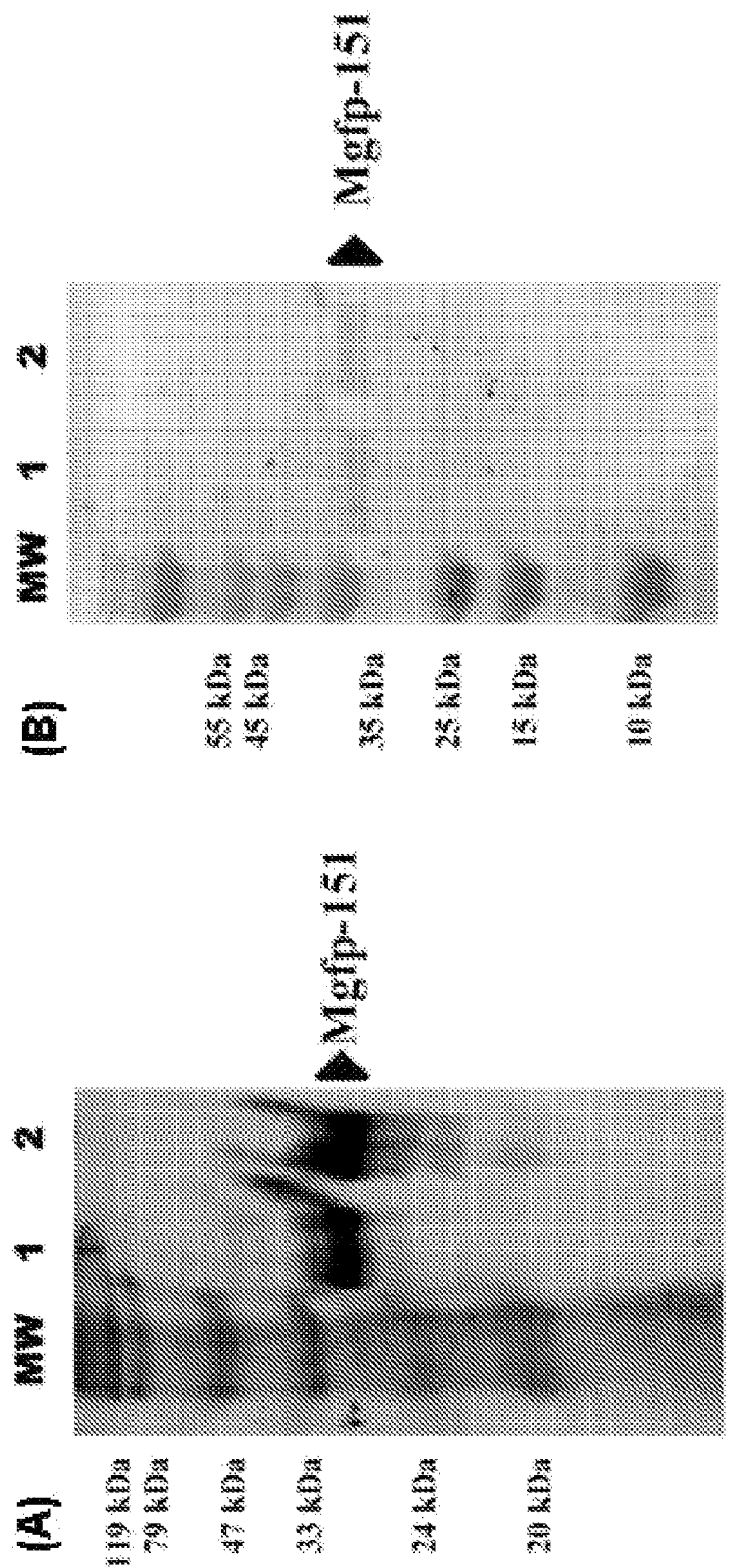
FIG. 17 shows (A) SDS-PAGE and (B) Western blot analyses of chromatographic fractions of recombinant MGFP-151 protein.

A 40 cm×2.6 cm column was filled with Sephacryl S-300 HR (Pharmacia), and equilibrated with 5% acetic acid. Afterwards, 2 ml of sample was loaded, and the sample was eluted with 5 (v/v) % acetic acid and eluted fractions I and II were collected. The degree of purification of MGFP-151 in eluted fractions I and II was confirmed by SDS-polyacylamide gel electrophoresis and then staining by Coomassie blue (FIG. 17). FIG. 17 shows photographs of SDS-PAGE analysis (A) and a Western blot analysis (B) of the chromatographic fractions of MGFP-151 recombinant protein. recombinant MGFP-151 protein with 95.8% purity could be isolated by chromatography.

The purified recombinant MGFP-151 protein was confirmed to be the same at the initially designed MGFP-151 peptide, through analysis with MALDI-TOF mass spectrometer.

EXAMPLE 10

Modification of the Adhesive Protein's Tyrosine Residues

The MGFP-5, MGFP-51, MGFP-15 and MGFP-151 adhesive proteins purified in Examples 6 to 9 were each dissolved to a concentration of 1.44 mg/ml in 5% acetic acid buffer containing 25 mM ascorbic acid. Then after the addition of 50 ug/ml of tyrosinase, it was shaken for 6 hours at 25° C. Through this process, the tyrosine residues of the adhesive proteins were modified to DOPA. Furthermore, bovine serum albumin (BSA) was used as negative control, and the commercial product Cell-Tak™ (BD Bioscience, Two Oak Park, Belford, Mass., USA) which consists of mussel adhesive proteins FP-1 and FP-2 was used as positive control.

EXAMPLE 11

Verification of the Ability of the Recombinant MGFP-5 and MGFP-151 Proteins to Coat Various Surfaces The abilities of recombinant MGFP-5 and MGFP-151 proteins to coat the surfaces of glass slide, poly(methyl methacrylate) plate, and aluminum plate were measured. Each material surface was cleaned by washing with water several times and drying with nitrogen gas. A 5 μl drop of 1.44 mg/ml protein solution was spotted onto each surface and kept for 12 h at 25° C. After drying, each surface was washed thoroughly with double distilled water for 2 h with shaking, and the water remaining on each surface was evaporated with a vacuum pump. After drying, the protein coated on the surface was visualized using Coomassie blue staining. This result is shown in FIG. 18.

Figure 18:
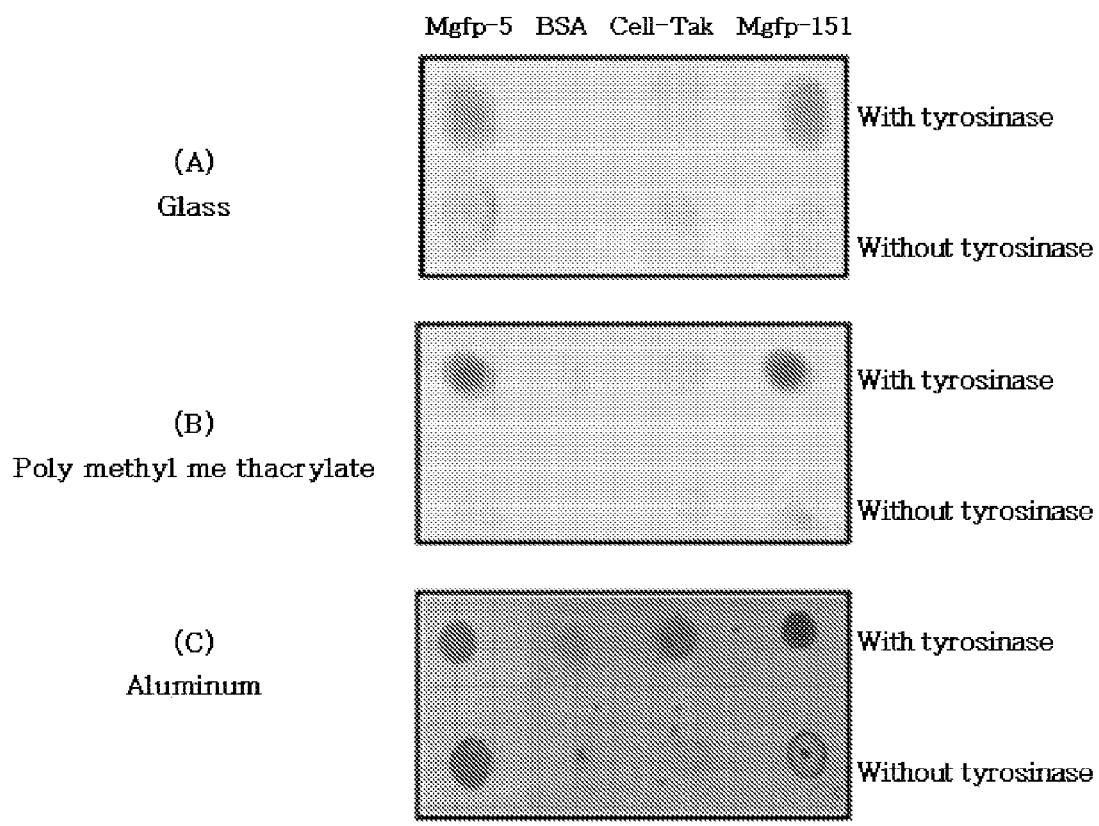
FIG. 18 shows the results of coating slide glass, poly(m-ethyl methacrylate) plate, and aluminum plate with recombinant MGFP-5 and recombinant MGFP-151 proteins after the tyrosine residues are modified to DOPA.

FIG. 18 shows the result of coating the surfaces of glass slide, poly(methyl methacrylate) plate, and aluminum plate with recombinant MGFP-5 and MGFP-151 proteins after their tyrosine residues are modified to DOPA. The recombinant MGFP-5 and MGFP-151 proteins adhered to glass, poly (methyl methacrylate), and aluminum even before modification of their tyrosine residues, and the adhesion force was found to be much higher when the tyrosine residues are modified to DOPA.

EXAMPLE 12

Measurement of Adsorption of Recombinant Adhesive Protein Using QCM (Quartz Crystal Microbalance)

The quartz crystal used (Seiko EG & G) was a gold-coated AT-cut quartz 5 mm in diameter with a basic resonant frequency of 9 MHz. A 5 μl drop of a 1.44 mg/ml protein solution (BSA, Cell-Tak, recombinant MGFP-5 protein, and recombinant MGFP-151 protein) was each placed onto the gold surface of the quartz crystal and kept at 25° C. in a constant-temperature water bath for 1 hour. After taking it out of the water bath and drying, the gold surface was rinsed thoroughly in double distilled water for 1 h with shaking and the water remaining on the quartz crystal was evaporated using a vacuum pump. Dried quartz crystal was connected to an EQCM controller (QCA917; Seiko EG & G) and variations in resonance frequency were measured. Since the resonance frequency of the quartz crystal decreases as a function of increase in the mass adsorbed on its surface (G. Sauerbrey, 1959, Z. Phys, 155, 206), the increase in mass was calculated by Equation 1 (M. Thomson, 1991, Analyst, 116, 881-889) with the value for change in resonance frequency.

$$\Delta mass = \frac{-\Delta freq \times A \times \sqrt{\mu_q \times \rho_q}}{2 \times F_q^2} \quad \text{(Equation 1)}$$

In the above Equation 1, Δmass is change in mass, Δfreq is change in resonance frequency, $\mu_q$ is AT-cut quartz crystal constant ($2.947 \times 1.011$ g/cm/sec$^2$), $P_q$ is the quartz crystal density (2.648 g/cm$^2$), $F_q^2$ is reference frequency (9.00 MHz), and A is quartz crystal surface area (0.196 cm$^2$).

Figure 19:
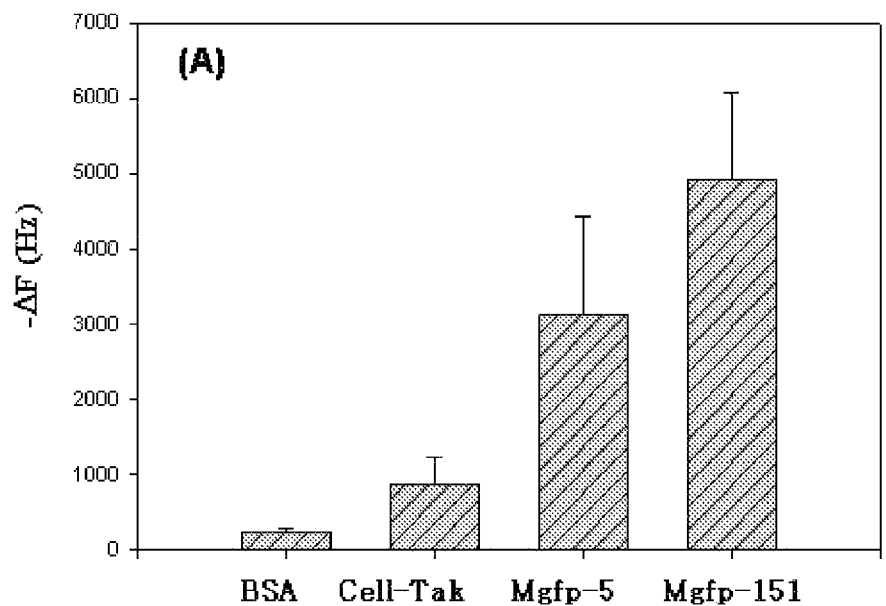
FIG. 19 shows the QCM analysis results of BSA, Cell-Tak, recombinant MGFP-5 protein, and recombinant MGFP-151 protein after treating the tyrosines.
Figure 19:
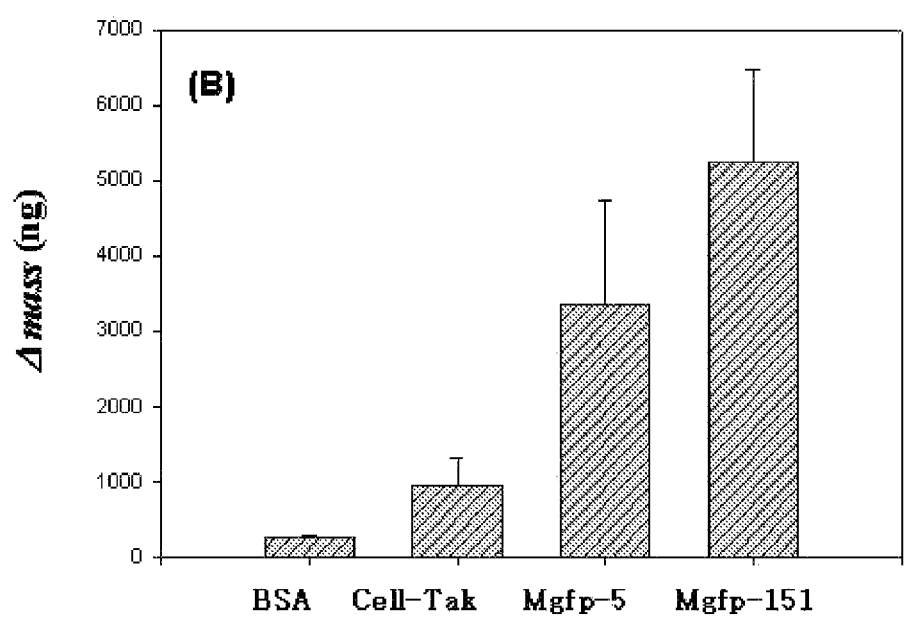

FIG. 19 is the result of QCM analysis of BSA, Cell-Tak, recombinant MGFP-5 protein and recombinant MGFP-151 protein where the tyrosines were treated, showing the level of adsorption onto the gold surface as change in frequency. In FIG. 19, recombinant MGFP-151 protein modified with tyrosinase showed the greatest change in frequency, indicating the greatest mass adsorbing to the gold surface of the quartz crystal. Although Cell-Tak™ adsorbed in a greater amount compared to BSA, its adhesion force was much lower compared to that of recombinant MGFP-5 protein. The change in mass of recombinant MGFP-151 protein was 36%, that of recombinant MGFP-5 protein was 23.2%, and that of Cell-Tak was 10% or less.

EXAMPLE 13

Measurement of Adhesion Force of Recombinant Adhesion Protein Using AFM (Atomic Force Microscopy)

Figure 20:
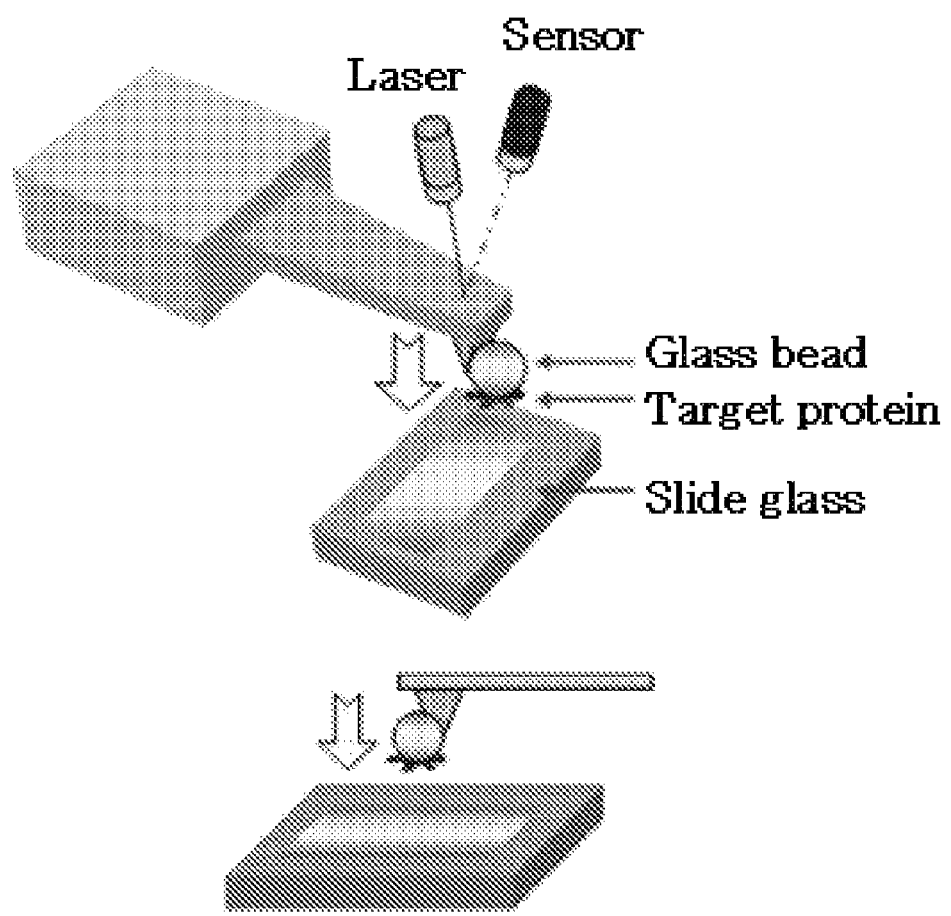
FIG. 20 is a diagram of the measurement method of the adhesion force of recombinant adhesive proteins.

The force-distance curve was obtained using AFM (SPA400; Seiko Instruments), and AFM cantilevers were done according to the technique of Ducker et al. (W. Ducker, Nature, 1991, 353, 239-241) (FIG. 20). The cantilevers used for the present experiments were Olympus oxide-sharpened silicon nitrate probes (Veeco & Seiko Instruments) and the spring constant was 0.57 or 11 N/m. A glass bead (Park Science) of 20 μm diameter was attached to the tip of the cantilever using an epoxy resin (Vantico), and kept at room temperature for 24 h. The AFM cantilevers with glass bead attached were mounted into the AFM, and the glass bead was immersed in 10 μl of tyrosinase-treated protein solutions (1.44 mg/ml BSA, Cell-Tak™, MGFP-1 or MGFP-5) (MGFP-5 or MGFP-151) for 10 min. The glass bead was brought into contact with clean glass surface, and a force-distance curve was obtained.

Figure 21:
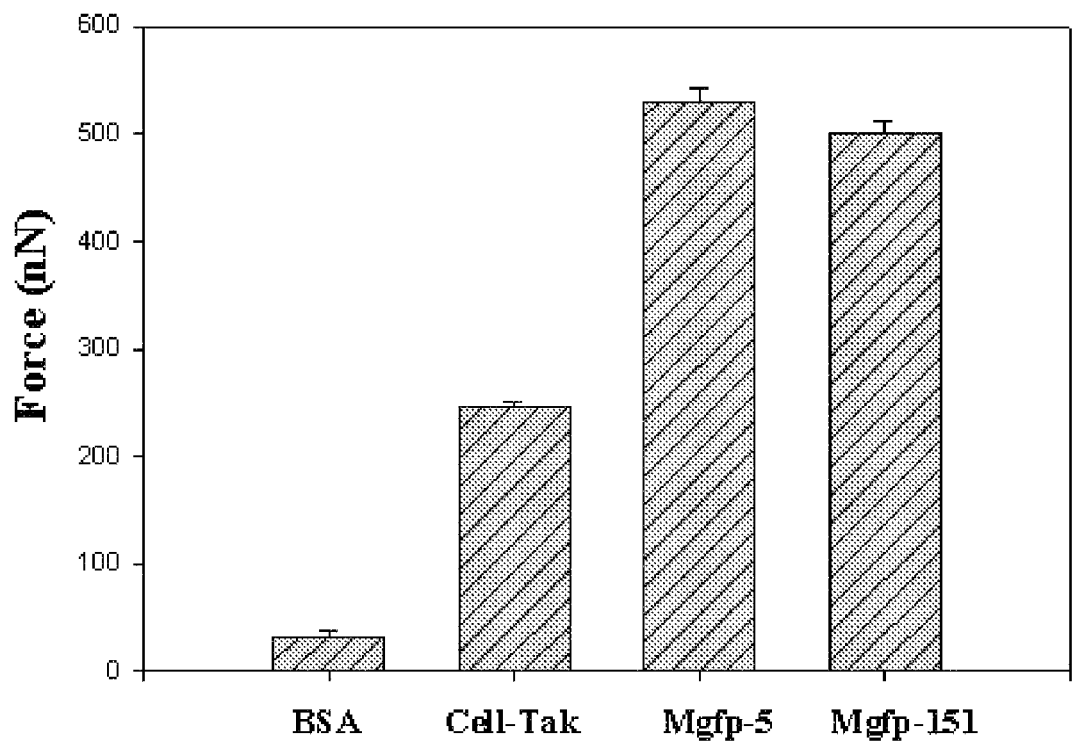
FIG. 21 shows the adhesion force of recombinant MGFP-1 and recombinant MGFP-5 proteins where the tyrosine residues have been modified.

FIG. 21 shows the adhesion force of recombinant MGFP-151 and MGFP-5 proteins with modified tyrosines. Recombinant mussel adhesive proteins MGFP-5 and MGFP-151 have average values of 540 nN and 500 nN respectively indicating strong adhesion force, whereas that of Cell-Tak was 250 nN, and that of BSA was around 30 nN. This result shows that tyrosinase-treated recombinant mussel adhesion proteins have strong adhesion ability.

EXAMPLE 14

Measurement of Cell Adhesion Property

*Drosophila* S2 Cells (Invitrogen) were Used.

S2 cells were grown at 27° C. in M3 medium (Shields and Sang M3 insect medium; Sigma, St. Louis, Mo.) containing 10% IMS (insect medium supplement), 1% antibiotic-antimycotic (Invitrogen), and hygromycin 3 μl/ml. Tyrosinase-treated recombinant MGFP-5 protein, recombinant MGFP-151 protein, Cell-Tak, and BSA prepared from Example 10 were dropped onto sterilized slide glass (20 mm×20 mm, Marienfeld, Germany) and incubated at 25° C. for 30 minutes in a laminar flow hood and then washed two times with PBS. After washing, the coated slide glass was immersed in 100-mm cell culture dishes containing S2 cells at a concentration of $4 \times 10^6$ cells/ml showing 95% viability. After incubation at 27° C. for 1 hr to 7 days, unattached cells were rinsed away with PBS, and cell viability and location of adhered protein was checked by trypan blue staining.

Figure 22:
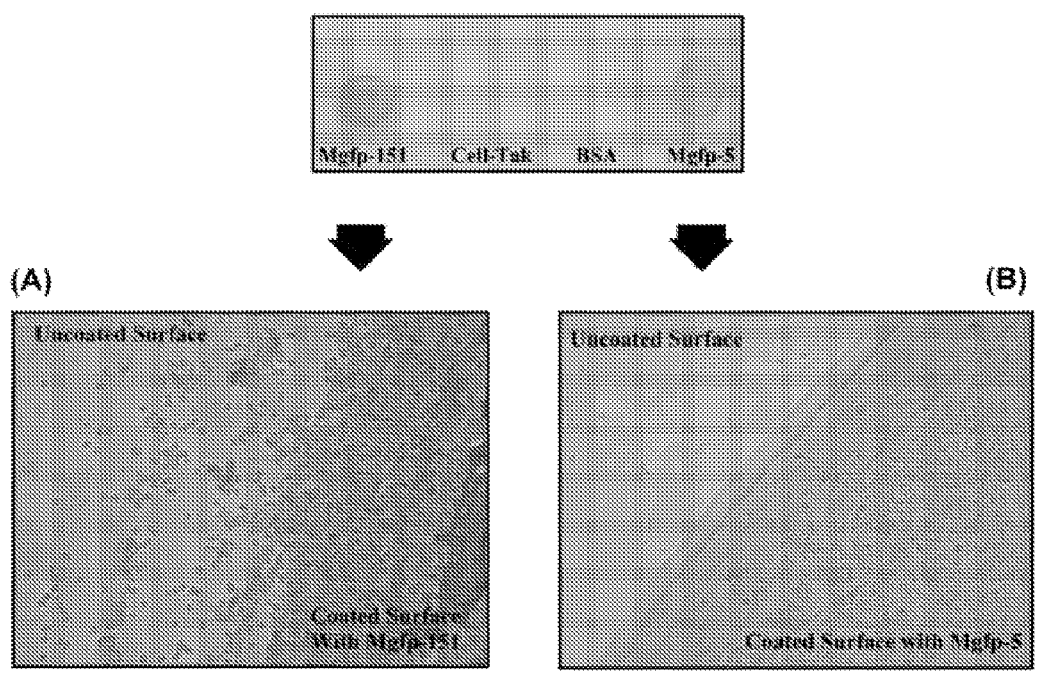
FIG. 22 is a measurement of cell-adhesion property of recombinant adhesive proteins.
Figure 23:
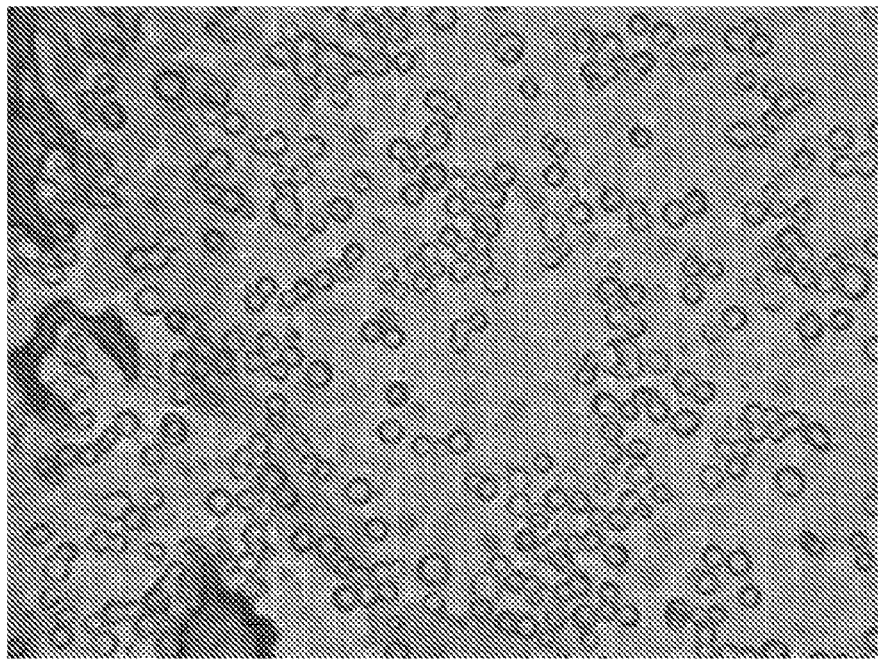
FIG. 23 is a measurement of cell-adhesion property of recombinant adhesive proteins with insect *Drosophila* S2 cells.
Figure 23:
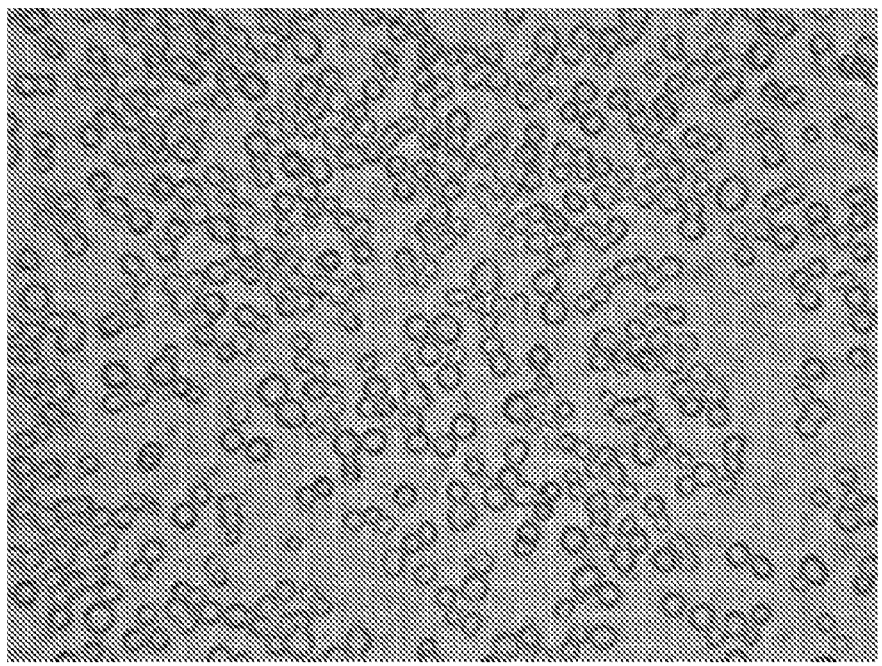

As a result, S2 cells were found to attach to regions where recombinant MGFP-5 and MGFP-151 proteins were coated, and the attached S2 cells survived for 7 days or more (FIGS. 22 and 23).

EXAMPLE 15

Examination of the Chemical Adhesive Stability of MGFP-5 and MGFP-151

The recombinant proteins MGFP-5 and MGFP-151 were each spotted onto glass and Cell-Tak was spotted on as control. After drying, it was immersed in a solution consisting of 5% acetic acid, 25% methanol, and 70% water, and heated for 20 minutes at 85° C. As a result, for the adhesive proteins coated on the surface of glass or acrylic plates, it was found that upon leaving at high temperatures under solvent conditions MGFP-5 became detached while MGFP-151 continued to stay attached.

Also, each was coated onto glass or acrylic plates and adhesive stability was measured through SEM.

Figure 24A:
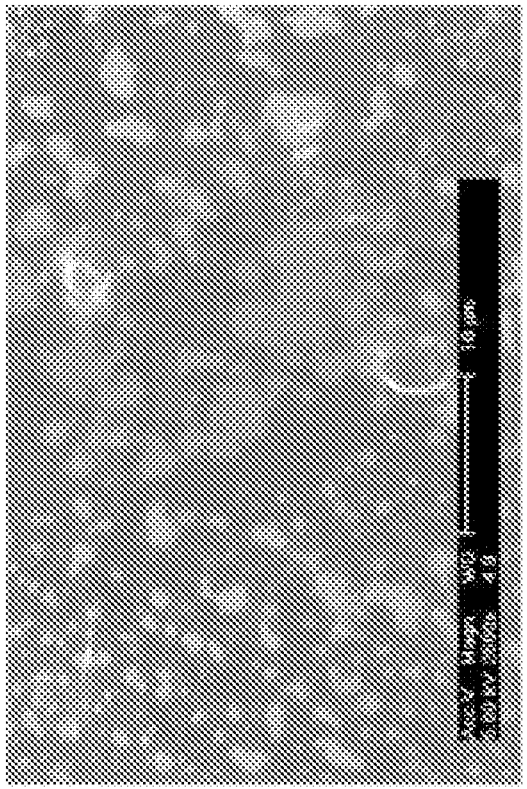
FIGS. 24A to C are photographs of a substrate surface coated with recombinant MGFP-5 and recombinant MGFP-151 proteins. A is a 2500× enlargement, B is a 10000× enlargement, and C is a 35000× enlargement.
Figure 24A:
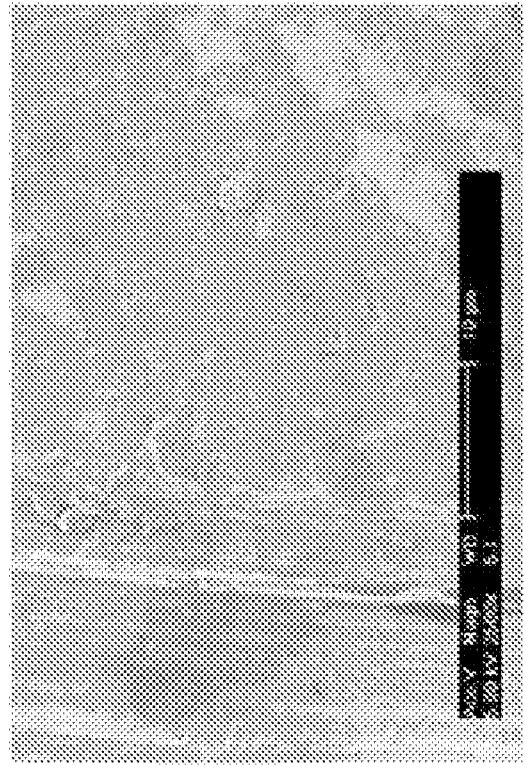
Figure 24B:
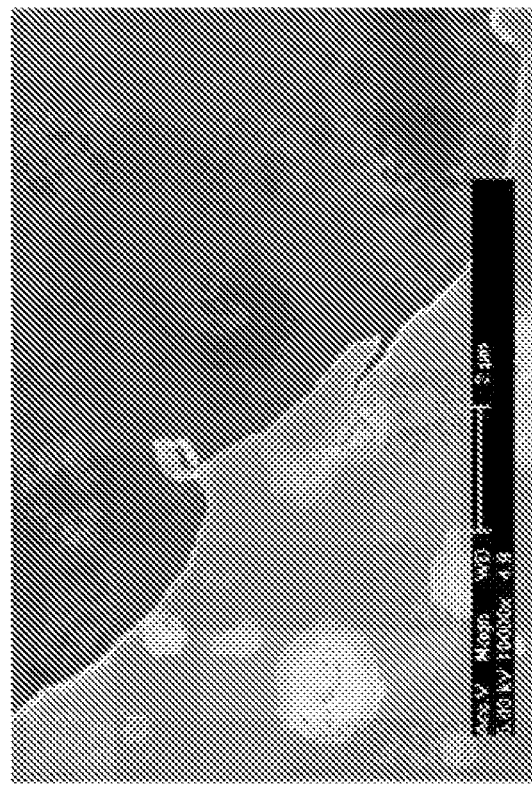
Figure 24B:
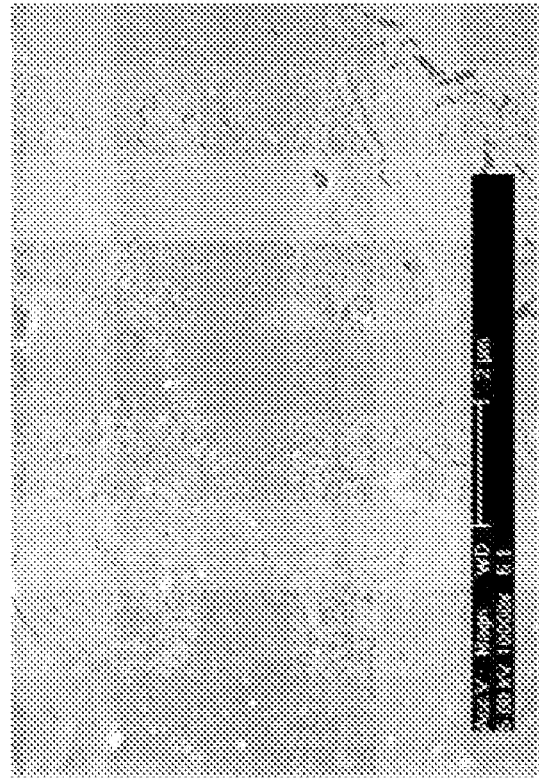
Figure 24C:
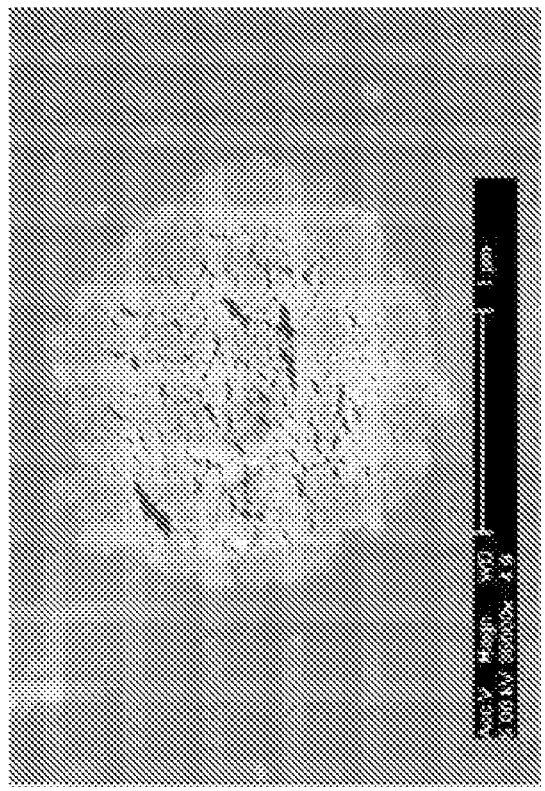
Figure 24C:
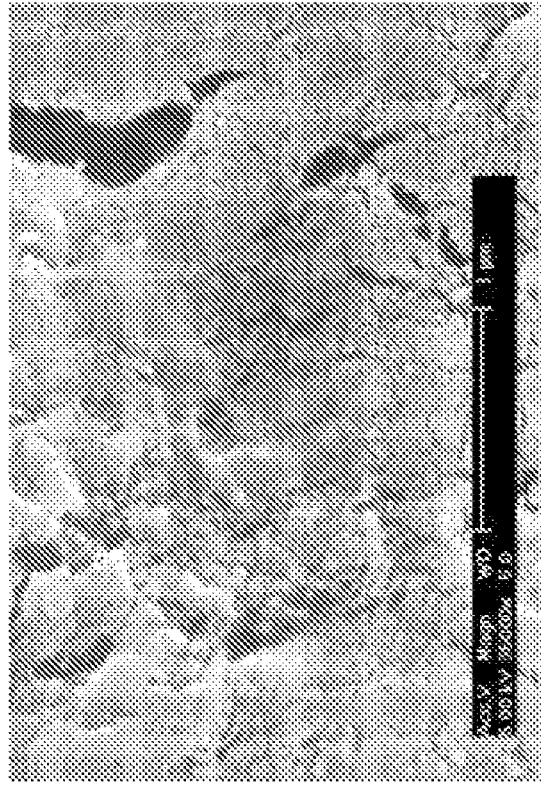

FIGS. 24A to C are photographs of the substrate surfaces coated with recombinant MGFP-5 and MGFP-151 proteins, where A is a 2500× enlargement, B is a 10000× enlargement, and C is a 35000× enlargement. On observation, the surface coated with MGFP-151 was found to be smooth, whereas the surface coated with MGFP-5 was found to be a little bit rough. This difference is thought to be a difference in the degree of cross-linking.

SEQUENCE LIST PRETEXT

SEQ ID NOs: 1 to 4 are primer sequences.

SEQ ID NO: 5 is the cDNA of MGFP-5 protein isolated from *Mytilus galloprovincialis*.

SEQ ID NO: 6 is the protein sequence of MGFP-5 protein isolated from *Mytilus galloprovincialis*.

SEQ ID NO: 7 is the nucleotide sequence of 6 tandem repeats of a partial sequence of MEFP-5 protein isolated from *Mytilus edulis*.

SEQ ID NO: 8 is the amino acid sequence of 6 tandem repeats of a partial sequence of MEFP-5 protein isolated from *Mytilus edulis*.

SEQ ID NO: 9 is the nucleotide sequence encoding the recombinant adhesive protein MGFP-15 constructed from FP-1 and MGFP-5.

SEQ ID NO: 10 is the amino acid sequence of the recombinant adhesive protein MGFP-15 constructed from FP-1 and MGFP-5.

SEQ ID NO: 11 is the nucleotide sequence encoding the recombinant adhesive protein MGFP-015 constructed from FP-1 and MGFP-5.

SEQ ID NO: 12 is the amino acid sequence of the recombinant adhesive protein MGFP-015 constructed from FP-1 and MGFP-5.

SEQ ID NO: 13 is the nucleotide sequence encoding the recombinant adhesive protein MGFP-151 constructed from FP-1 and MGFP-5.

SEQ ID NO: 14 is the amino acid sequence of the recombinant adhesive protein MGFP-151 constructed from FP-1 and MGFP-5.

SEQ ID NO: 15 is the nucleotide sequence of the construct inserted into the pMDG05 vector for the expression of MGFP-5.

SEQ ID NO: 16 is the amino acid sequence of the adhesive protein expressed from the construct inserted into the pMDG05 vector for the expression of MGFP-5.

SEQ ID NO: 17 is the nucleotide sequence of the construct inserted into the pMDG150 vector for the expression of MGFP-15.

SEQ ID NO: 18 is the amino acid sequence of the adhesive protein expressed from the construct inserted into the pMDG150 vector for the expression of MGFP-15.

SEQ ID NO: 19 is the nucleotide sequence of the construct inserted into the pMDG051 vector for the expression of MGFP-51.

SEQ ID NO: 20 is the amino acid sequence of the adhesive protein expressed from the construct inserted into the pMDG051 vector for the expression of MGFP-51.

SEQ ID NO: 21 is the nucleotide sequence of the construct inserted into the pMDG151 vector for the expression of MGFP-151.

SEQ ID NO: 22 is the amino acid sequence of the adhesive protein expressed from the construct inserted into the pMDG151 vector for the expression of MGFP-151.

SEQ ID Nos: 23 to 24 are primer sequences.

SEQ ID NO: 25 is a partial sequence of FP-1.

SEQ ID Nos: 26 to 31 are nucleotide sequences encoding AKPSYPPTYK which is a partial sequence of FP-1.

SEQ ID NO: 32 is the primer sequence of the T3 promoter.

SEQ ID NO: 33 is the primer sequence of the T7 promoter.

SEQ ID Nos: 34 to 35 are primer sequences.

---

What is claimed is:

1. An adhesive protein comprising SEQ ID NO: 6.

2. The adhesive protein of claim 1, wherein the adhesive protein further comprises a peptide of SEQ ID NO: 25 tandemly repeated 1 to 10 times.

3. The adhesive protein of claim 2, wherein the adhesive protein comprises an amino acid selected from the group consisting of SEQ ID NO: 10, SEQ ID NO: 12, and SEQ ID NO: 14.

4. The adhesive protein of claim 1, wherein the adhesive protein further comprises a peptide which comprises 6 histidine tags.

5. The adhesive protein of claim 4, wherein the adhesive protein comprises an amino acid sequence selected from the group consisting of SEQ ID NO: 16, SEQ ID NO: 18, SEQ ID NO: 20, and SEQ ID NO: 22.

6. An adhesive comprising an adhesive protein according to claim 3 as an active component.

7. The adhesive of claim 6, wherein 5% to 100% of the total number of tyrosine residues in the adhesive protein is modified to 3,4-dihydroxyphenyl-L-alanine (DOPA).

8. The adhesive of claim 6, wherein the adhesive adheres to a substrate selected from the group consisting of plastic, glass, metal, eukaryotic cells, prokaryotic cells, and plant cell walls and lipids.

9. The adhesive of claim 6, wherein the adhesive is applied to biological sample.

10. The adhesive of claim 6, wherein the adhesive further comprises one or more material selected from the group consisting of surfactant, oxidant, and filler.

11. The adhesive of claim 10, wherein the filler is selected from the group consisting of collagen, hyaluronic acid, condroitan sulfate, elastine, laminin, caseine, hydroxyapatite, and albumin, fibronectin, and hybrin.

12. The adhesive of claim 6, wherein the adhesive is applied to substrates used in an underwater environment.

13. A coating agent containing an adhesive protein according to claim 3 as an active component.

* * * * *

SEQUENCE LISTING

```
<160> NUMBER OF SEQ ID NOS: 35

<210> SEQ ID NO 1
<211> LENGTH: 30
<212> TYPE: DNA
<213> ORGANISM: Artificial Sequence
<220> FEATURE:
<223> OTHER INFORMATION: primer

<400> SEQUENCE: 1
ggcctgcagc agttctgaag aatacaaggg                               30

<210> SEQ ID NO 2
<211> LENGTH: 29
<212> TYPE: DNA
<213> ORGANISM: Artificial Sequence
<220> FEATURE:
<223> OTHER INFORMATION: primer
```

-continued

<400> SEQUENCE: 2
gtagatctat acgccggacc agtgaacag                              29

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3 cttgtattttt ccgctgtttt t                                      21

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
aaaaacagcg gaaaatacaa g                                       21

<210> SEQ ID NO 5
<211> LENGTH: 228
<212> TYPE: DNA
<213> ORGANISM: Artificial Sequence
<220> FEATURE:
<223> OTHER INFORMATION: Mytilus galloprovincialis

<400> SEQUENCE: 5
agttctgaag aatacaaagg tggttattac ccaggcaata cttaccacta tcattcaggt    60
ggtagttatc acggatccgg ctatcatgga ggatataagg gaaagtatta cggaaaggca   120
aagaaatact attataaata taaaaacagc ggaaaataca agtatctgaa gaaagctaga   180
aaataccata gaaagggtta caagaagtat tatggaggtg gtagcagt              228

<210> SEQ ID NO 6
<211> LENGTH: 76
<212> TYPE: PRT
<213> ORGANISM: Artificial Sequence
<220> FEATURE:
<223> OTHER INFORMATION: Mytilus galloprovincialis

<400> SEQUENCE: 6

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
50                  55                  60

Lys Gly Tyr Lys Lys Tyr Tyr Gly Gly Gly Ser Ser
65                  70                  75

<210> SEQ ID NO 7
<211> LENGTH: 180
<212> TYPE: DNA
<213> ORGANISM: Artificial Sequence
<220> FEATURE:
<223> OTHER INFORMATION: mytilus edulis

```
<400> SEQUENCE: 7
gctaaaccgt cttacccgcc gacctacaaa gcaaaaccct cgtacccacc gacttataag      60
gctaaaccta gctatccacc tacgtacaaa gctaaaccgt cttacccgcc gacttacaaa     120
gcaaaaccgt cctaccctcc gacctataag gctaaaccga gttaccccccc gacttacaaa    180

<210> SEQ ID NO 8
<211> LENGTH: 60
<212> TYPE: PRT
<213> ORGANISM: Artificial Sequence
<220> FEATURE:
<223> OTHER INFORMATION: mytilus edulis

<400> SEQUENCE: 8

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys
    50                  55                  60

<210> SEQ ID NO 9
<211> LENGTH: 411
<212> TYPE: DNA
<213> ORGANISM: Artificial Sequence
<220> FEATURE:
<223> OTHER INFORMATION: Bioadhesive protein(mgfp-150)

<400> SEQUENCE: 9
gctaaaccgt cttacccgcc gacctacaaa gcaaaaccct cgtacccacc gacttataag      60
gctaaaccta gctatccacc tacgtacaaa gctaaaccgt cttacccgcc gacttacaaa     120
gcaaaaccgt cctaccctcc gacctataag gctaaaccga gttaccccccc gacttacaaa    180 agttctgaag aatacaaggg tggttattac ccaggcaatt cgaaccacta tcattcaggt     240
ggtagttatc acggatccgg ctaccatgga ggatataagg aaagtatta cggaaaggca     300 aagaaatact attataaata taaaaacagc ggaaaataca agtatctaaa gaaagctaga     360
aaataccata gaagggttta caagaagtat tatggaggta gcagtgaatt c             411

<210> SEQ ID NO 10
<211> LENGTH: 137
<212> TYPE: PRT
<213> ORGANISM: Artificial Sequence
<220> FEATURE:
<223> OTHER INFORMATION: Bioadhesive protein(mgfp-150)

<400> SEQUENCE: 10

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys Ser Ser Glu Glu
    50                  55                  60

Tyr Lys Gly Gly Tyr Tyr Pro Gly Asn Ser Asn His Tyr His Ser Gly
65                  70                  75                  80
```

```
Gly Ser Tyr His Gly Ser Gly Tyr His Gly Gly Tyr Lys Gly Lys Tyr
        85                  90                  95

Tyr Gly Lys Ala Lys Lys Tyr Tyr Lys Tyr Lys Asn Ser Gly Lys
100                 105                 110

Tyr Lys Tyr Leu Lys Lys Ala Arg Lys Tyr His Arg Lys Gly Tyr Lys
115                 120                 125

Lys Tyr Tyr Gly Gly Ser Ser Glu Phe
130                 135

<210> SEQ ID NO 11
<211> LENGTH: 411
<212> TYPE: DNA
<213> ORGANISM: Artificial Sequence
<220> FEATURE:
<223> OTHER INFORMATION: Bioadhesive protein(mgfp-051)

<400> SEQUENCE: 11
agttctgaag aatacaaggg tggttattac ccaggcaatt cgaaccacta tcattcaggt     60
ggtagttatc acggatccgg ctaccatgga ggatataagg gaaagtatta cggaaaggca    120
aagaaatact attataaata taaaaacagc ggaaaataca agtatctaaa gaaagctaga    180
aaataccata gaagggttaa caagaagtat tatggaggta gcagtgaatt cgctaaaccg    240
tcttacccgc cgacctacaa agcaaaaccc tcgtacccac cgacttataa ggctaaacct    300
agctatccac ctacgtacaa agctaaaccg tcttacccgc cgacttacaa agcaaaaccg    360
tcctaccctc cgacctataa ggctaaaccg agttaccccc cgacttacaa a             411

<210> SEQ ID NO 12
<211> LENGTH: 137
<212> TYPE: PRT
<213> ORGANISM: Artificial Sequence
<220> FEATURE:
<223> OTHER INFORMATION: Bioadhesive protein(mgfp-051)

<400> SEQUENCE: 12

Ser Ser Glu Glu Tyr Lys Gly Gly Tyr Tyr Pro Gly Asn Ser Asn His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Lys Tyr Lys
35                  40                  45

Asn Ser Gly Lys Tyr Lys Tyr Leu Lys Lys Ala Arg Lys Tyr His Arg
50                  55                  60

Lys Gly Tyr Lys Lys Tyr Tyr Gly Gly Ser Ser Glu Phe Ala Lys Pro
65                  70                  75                  80

Ser Tyr Pro Pro Thr Tyr Lys Ala Lys Pro Ser Tyr Pro Pro Thr Tyr
            85                  90                  95

Lys Ala Lys Pro Ser Tyr Pro Pro Thr Tyr Lys Ala Lys Pro Ser Tyr
100                 105                 110

Pro Pro Thr Tyr Lys Ala Lys Pro Ser Tyr Pro Pro Thr Tyr Lys Ala
115                 120                 125

Lys Pro Ser Tyr Pro Pro Thr Tyr Lys
130                 135

<210> SEQ ID NO 13
<211> LENGTH: 591
<212> TYPE: DNA
<213> ORGANISM: Artificial Sequence
<220> FEATURE:
```

-continued

<223> OTHER INFORMATION: Bioadhesive protein(mgfp-151)

<400> SEQUENCE: 13

```
gctaaaccgt cttacccgcc gacctacaaa gcaaaaccct cgtacccacc gacttataag    60
gctaaaccta gctatccacc tacgtacaaa gctaaaccgt cttacccgcc gacttacaaa   120
gcaaaaccgt cctaccctcc gacctataag gctaaaccga gttaccccgc gacttacaaa   180
agttctgaag aatacaaggg tggttattac ccaggcaatt cgaaccacta tcattcaggt   240
ggtagttatc acggatccgg ctaccatgga ggatataagg gaaagtatta cggaaaggca   300
aagaaatact attataaata taaaaacagc ggaaaataca agtatctaaa gaaagctaga   360
aaataccata gaaagggtta caagaagtat tatggaggta gcagtgaatt cgctaaaccg   420
tcttacccgc cgacctacaa agcaaaaccc tcgtacccac cgacttataa ggctaaacct   480
agctatccac ctacgtacaa agctaaaccg tcttacccgc cgacttacaa agcaaaaccg   540
tcctaccctc cgacctataa ggctaaaccg agttaccccc cgacttacaa a            591
```

<210> SEQ ID NO 14
<211> LENGTH: 197
<212> TYPE: PRT
<213> ORGANISM: Artificial Sequence
<220> FEATURE:
<223> OTHER INFORMATION: Bioadhesive protein(mgfp-151)

<400> SEQUENCE: 14

```
Ala Lys Pro Ser Tyr Pro Pro Thr Tyr Lys Ala Lys Pro Ser Tyr Pro
1               5                   10                  15
Pro Thr Tyr Lys Ala Lys Pro Ser Tyr Pro Pro Thr Tyr Lys Ala Lys
            20                  25                  30
Pro Ser Tyr Pro Pro Thr Tyr Lys Ala Lys Pro Ser Tyr Pro Pro Thr
        35                  40                  45
Tyr Lys Ala Lys Pro Ser Tyr Pro Pro Thr Tyr Lys Ser Ser Glu Glu
    50                  55                  60
Tyr Lys Gly Gly Tyr Tyr Pro Gly Asn Ser Asn His Tyr His Ser Gly
65                  70                  75                  80
Gly Ser Tyr His Gly Ser Gly Tyr His Gly Gly Tyr Lys Gly Lys Tyr
                85                  90                  95
Tyr Gly Lys Ala Lys Lys Tyr Tyr Tyr Lys Tyr Lys Asn Ser Gly Lys
            100                 105                 110
Tyr Lys Tyr Leu Lys Lys Ala Arg Lys Tyr His Arg Lys Gly Tyr Lys
        115                 120                 125
Lys Tyr Tyr Gly Gly Ser Ser Glu Phe Ala Lys Pro Ser Tyr Pro Pro
    130                 135                 140
Thr Tyr Lys Ala Lys Pro Ser Tyr Pro Pro Thr Tyr Lys Ala Lys Pro
145                 150                 155                 160
Ser Tyr Pro Pro Thr Tyr Lys Ala Lys Pro Ser Tyr Pro Pro Thr Tyr
                165                 170                 175
Lys Ala Lys Pro Ser Tyr Pro Pro Thr Tyr Lys Ala Lys Pro Ser Tyr
            180                 185                 190
Pro Pro Thr Tyr Lys
        195
```

<210> SEQ ID NO 15
<211> LENGTH: 339
<212> TYPE: DNA
<213> ORGANISM: Artificial Sequence
<220> FEATURE:

<223> OTHER INFORMATION: construct for expression of Bioadhesive
      protein(mgfp-5) in pMDG05 vector

<400> SEQUENCE: 15

```
atgggggtt ctcatcatca tcatcatcat ggtatggcta gcatgactgg tggacagcaa      60
atgggtcgga ctctgtacga cgatgacgat aaggatcgat ggggatccga gctcgagatc    120
tgcagcagtt ctgaagaata caagggtggt tattacccag gcaattcgaa ccactatcat    180
tcaggtggta gttatcacgg atccggctac catggaggat ataagggaaa gtattacgga    240
aaggcaaaga aatactatta taaatataaa aacagcggaa aatacaagta tctaaagaaa    300
gctagaaaat accatagaaa gggttacaag aagtattat                            339
```

<210> SEQ ID NO 16
<211> LENGTH: 117
<212> TYPE: PRT
<213> ORGANISM: Artificial Sequence
<220> FEATURE:
<223> OTHER INFORMATION: Bioadhesive recombinant protein expressed in
      pMDG05 vector

<400> SEQUENCE: 16

```
Met Gly Gly Ser His His His His His Gly Met Ala Ser Met Thr
1               5                   10                  15

Gly Gly Gln Gln Met Gly Arg Thr Leu Tyr Asp Asp Asp Lys Asp
            20                  25                  30

Arg Trp Gly Ser Glu Leu Glu Ile Cys Ser Ser Ser Glu Glu Tyr Lys
35                  40                  45

Gly Gly Tyr Tyr Pro Gly Asn Ser Asn His Tyr His Ser Gly Gly Ser
50                  55                  60

Tyr His Gly Ser Gly Tyr His Gly Gly Tyr Lys Gly Lys Tyr Tyr Gly
65                  70                  75                  80

Lys Ala Lys Lys Tyr Tyr Tyr Lys Tyr Lys Asn Ser Gly Lys Tyr Lys
                85                  90                  95

Tyr Leu Lys Lys Ala Arg Lys Tyr His Arg Lys Gly Tyr Lys Lys Tyr
                100                 105                 110

Tyr Gly Gly Ser Ser
115
```

<210> SEQ ID NO 17
<211> LENGTH: 435
<212> TYPE: DNA
<213> ORGANISM: Artificial Sequence
<220> FEATURE:
<223> OTHER INFORMATION: construct for expression of Bioadhesive
      protein(mgfp-150) in pMDG150 vector

<400> SEQUENCE: 17

```
atgggggtt ctcatcatca tcatcatcat ggtatggcta gcgctaaacc gtcttacccg      60
ccgacctaca agcaaaaacc ctcgtaccca ccgacttata aggctaaacc tagctatcca    120
cctacgtaca agctaaaacc gtcttacccg ccgacttaca agcaaaaacc gtcctaccct    180
ccgacctata aggctaaacc gagttacccc ccgacttaca aggctgcag ttctgaagaa    240 tacaagggtg ttattaccc aggcaattcg aaccactatc attcaggtgg tagttatcac    300
ggatccggct accatggagg atataaggga agtattacg gaaaggcaaa gaaatactat    360
tataaatata aaaacagcgg aaaatacaag tatctaaaga agctagaaaa ataccataga    420
aagggttaca agaag                                                    435
```

<210> SEQ ID NO 18
<211> LENGTH: 151
<212> TYPE: PRT
<213> ORGANISM: Artificial Sequence
<220> FEATURE:
<223> OTHER INFORMATION: Bioadhesive recombinant protein expressed in
      pMDG150 vector

<400> SEQUENCE: 18

```
Met Gly Gly Ser His His His His His Gly Met Ala Ser Ala Lys
1               5                   10                  15

Pro Ser Tyr Pro Pro Thr Tyr Lys Ala Lys Pro Ser Tyr Pro Pro Thr
        20                  25                  30

Tyr Lys Ala Lys Pro Ser Tyr Pro Pro Thr Tyr Lys Ala Lys Pro Ser
35                  40                  45

Tyr Pro Pro Thr Tyr Lys Ala Lys Pro Ser Tyr Pro Pro Thr Tyr Lys
50                  55                  60

Ala Lys Pro Ser Tyr Pro Pro Thr Tyr Lys Gly Cys Ser Ser Glu Glu
65                  70                  75                  80

Tyr Lys Gly Gly Tyr Tyr Pro Gly Asn Ser Asn His Tyr His Ser Gly
                85                  90                  95

Gly Ser Tyr His Gly Ser Gly Tyr His Gly Gly Tyr Lys Gly Lys Tyr
100                 105                 110

Tyr Gly Lys Ala Lys Lys Tyr Tyr Tyr Lys Tyr Lys Asn Ser Gly Lys
115                 120                 125

Tyr Lys Tyr Leu Lys Lys Ala Arg Lys Tyr His Arg Lys Gly Tyr Lys
130                 135                 140

Lys Tyr Tyr Gly Gly Ser Ser
145                 150
```

<210> SEQ ID NO 19
<211> LENGTH: 531
<212> TYPE: DNA
<213> ORGANISM: Artificial Sequence
<220> FEATURE:
<223> OTHER INFORMATION: construct for expression of Bioadhesive
      protein(mgfp-051) in pMDG051 vector

<400> SEQUENCE: 19

```
atgggggtt ctcatcatca tcatcatcat ggtatggcta gcatgactgg tggacagcaa    60
atgggtcgga ctctgtacga cgatgacgat aaggatcgat ggggatccga gctcgagatc   120
tgcagcagtt ctgaagaata caaggtggt tattacccag caattcgaa ccactatcat    180 tcaggtggta gttatcacgg atccggctac catggaggat ataagggaaa gtattacgga   240
aaggcaaaga aatactatta taaatataaa acagcggaa atacaagta tctaaagaaa    300 gctagaaaat accatagaaa gggttacaag aagtattatg gaggtagcag tgaattcgct   360
aaaccgtctt acccgccgac ctacaaagca aaaccctcgt acccaccgac ttataaggct   420
aaacctagct atccacctac gtacaaagct aaaccgtctt acccgccgac ttacaaagca   480
aaaccgtcct acccctccgac ctataaggct aaaccgagtt accccccgac t            531
```

<210> SEQ ID NO 20
<211> LENGTH: 179
<212> TYPE: PRT
<213> ORGANISM: Artificial Sequence
<220> FEATURE:
<223> OTHER INFORMATION: Bioadhesive recombinant protein expressed in
      pMDG051 vector

```
<400> SEQUENCE: 20

Met Gly Gly Ser His His His His His Gly Met Ala Ser Met Thr
1               5                   10                  15

Gly Gly Gln Gln Met Gly Arg Thr Leu Tyr Asp Asp Asp Lys Asp
        20                  25                  30

Arg Trp Gly Ser Glu Leu Glu Ile Cys Ser Ser Ser Glu Glu Tyr Lys
35                  40                  45

Gly Gly Tyr Tyr Pro Gly Asn Ser Asn His Tyr His Ser Gly Gly Ser
50                  55                  60

Tyr His Gly Ser Gly Tyr His Gly Gly Tyr Lys Gly Lys Tyr Tyr Gly
65                  70                  75                  80

Lys Ala Lys Lys Tyr Tyr Tyr Lys Tyr Lys Asn Ser Gly Lys Tyr Lys
        85                  90                  95

Tyr Leu Lys Lys Ala Arg Lys Tyr His Arg Lys Gly Tyr Lys Lys Tyr
100                 105                 110

Tyr Gly Gly Ser Ser Glu Phe Ala Lys Pro Ser Tyr Pro Pro Thr Tyr
115                 120                 125

Lys Ala Lys Pro Ser Tyr Pro Pro Thr Tyr Lys Ala Lys Pro Ser Tyr
130                 135                 140

Pro Pro Thr Tyr Lys Ala Lys Pro Ser Tyr Pro Pro Thr Tyr Lys Ala
145                 150                 155                 160

Lys Pro Ser Tyr Pro Pro Thr Tyr Lys Ala Lys Pro Ser Tyr Pro Pro
165                 170                 175

Thr Tyr Lys

<210> SEQ ID NO 21
<211> LENGTH: 639
<212> TYPE: DNA
<213> ORGANISM: Artificial Sequence
<220> FEATURE:
<223> OTHER INFORMATION: construct for expression of Bioadhesive
      protein(mgfp-151) in pMDG151 vector

<400> SEQUENCE: 21 atgggggggtt ctcatcatca tcatcatcat ggtatggcta gcgctaaacc gtcttacccg      60
ccgacctaca aagcaaaaacc ctcgtaccca ccgacttata aggctaaacc tagctatcca     120
cctacgtaca agctaaaacc gtcttacccg ccgacttaca aagcaaaacc gtcctaccct     180
ccgacctata aggctaaacc gagttacccc ccgacttaca aaggctgcag ttctgaagaa     240
tacaagggtg gttattaccc aggcaattcg aaccactatc attcaggtgg tagttatcac     300
ggatccggct accatggagg atataaggga agtattacg gaaaggcaaa gaaatactat     360
tataaatata aaaacagcgg aaaatacaag tatctaaaga agctagaaa ataccataga     420 aagggttaca gaagtattaa tggaggtagc agtgaattcg ctaaaccgtc ttacccgccg     480
acctacaaag caaaaccctc gtacccaccg acttataagg ctaaacctag ctatccacct     540
acgtacaaag ctaaaaccgtc ttacccgccg acttacaaag caaaaccgtc ctaccctccg     600
acctataagg ctaaaccgag ttaccccccg acttacaaa                             639

<210> SEQ ID NO 22
<211> LENGTH: 213
<212> TYPE: PRT
<213> ORGANISM: Artificial Sequence
<220> FEATURE:
<223> OTHER INFORMATION: construct for expression of Bioadhesive
      protein(mgfp-151) in pMDG151 vector
```

```
<400> SEQUENCE: 22

Met Gly Gly Ser His His His His His Gly Met Ala Ser Ala Lys
1               5                   10                  15

Pro Ser Tyr Pro Pro Thr Tyr Lys Ala Lys Pro Ser Tyr Pro Pro Thr
            20                  25                  30

Tyr Lys Ala Lys Pro Ser Tyr Pro Pro Thr Tyr Lys Ala Lys Pro Ser
35                  40                  45

Tyr Pro Pro Thr Tyr Lys Ala Lys Pro Ser Tyr Pro Pro Thr Tyr Lys
50                  55                  60

Ala Lys Pro Ser Tyr Pro Pro Thr Tyr Lys Gly Cys Ser Ser Glu Glu
65                  70                  75                  80

Tyr Lys Gly Gly Tyr Tyr Pro Gly Asn Ser Asn His Tyr His Ser Gly
85                  90                  95

Gly Ser Tyr His Gly Ser Gly Tyr His Gly Gly Tyr Lys Gly Lys Tyr
100                 105                 110

Tyr Gly Lys Ala Lys Lys Tyr Tyr Lys Tyr Lys Asn Ser Gly Lys
115                 120                 125

Tyr Lys Tyr Leu Lys Lys Ala Arg Lys Tyr His Arg Lys Gly Tyr Lys
130                 135                 140

Lys Tyr Tyr Gly Gly Ser Ser Glu Phe Ala Lys Pro Ser Tyr Pro Pro
145                 150                 155                 160

Thr Tyr Lys Ala Lys Pro Ser Tyr Pro Pro Thr Tyr Lys Ala Lys Pro
165                 170                 175

Ser Tyr Pro Pro Thr Tyr Lys Ala Lys Pro Ser Tyr Pro Pro Thr Tyr
180                 185                 190

Lys Ala Lys Pro Ser Tyr Pro Pro Thr Tyr Lys Ala Lys Pro Ser Tyr
195                 200                 205

Pro Pro Thr Tyr Lys
210

<210> SEQ ID NO 23
<211> LENGTH: 28
<212> TYPE: DNA
<213> ORGANISM: Artificial Sequence
<220> FEATURE:
<223> OTHER INFORMATION: primer

<400> SEQUENCE: 23
ggtacccgaa ttcgaattcg ctaaaccg                                28

<210> SEQ ID NO 24
<211> LENGTH: 30
<212> TYPE: DNA
<213> ORGANISM: Artificial Sequence
<220> FEATURE:
<223> OTHER INFORMATION: primer

<400> SEQUENCE: 24
ggtcgactca agcttatcat ttgtaagtcg                              30

<210> SEQ ID NO 25
<211> LENGTH: 10
<212> TYPE: PRT
<213> ORGANISM: Artificial Sequence
<220> FEATURE:
<223> OTHER INFORMATION: mytilus edulis

<400> SEQUENCE: 25

Ala Lys Pro Ser Tyr Pro Pro Thr Tyr Lys
```

```
              1               5                    10
```

<210> SEQ ID NO 26
<211> LENGTH: 30
<212> TYPE: DNA
<213> ORGANISM: Artificial Sequence
<220> FEATURE:
<223> OTHER INFORMATION: Mytilus edulis

<400> SEQUENCE: 26
gctaaaccgt cttacccgcc gacctacaaa                                        30

<210> SEQ ID NO 27
<211> LENGTH: 30
<212> TYPE: DNA
<213> ORGANISM: Artificial Sequence
<220> FEATURE:
<223> OTHER INFORMATION: Mytilus edulis

<400> SEQUENCE: 27
gcaaaaccct cgtacccacc gacttataag                                        30

<210> SEQ ID NO 28
<211> LENGTH: 30
<212> TYPE: DNA
<213> ORGANISM: Artificial Sequence
<220> FEATURE:
<223> OTHER INFORMATION: Mytilus edulis

<400> SEQUENCE: 28
gctaaaccta gctatccacc tacgtacaaa                                        30

<210> SEQ ID NO 29
<211> LENGTH: 30
<212> TYPE: DNA
<213> ORGANISM: Artificial Sequence
<220> FEATURE:
<223> OTHER INFORMATION: Mytilus edulis

<400> SEQUENCE: 29
gctaaaccgt cttacccgcc gacttacaaa                                        30

<210> SEQ ID NO 30
<211> LENGTH: 30
<212> TYPE: DNA
<213> ORGANISM: Artificial Sequence
<220> FEATURE:
<223> OTHER INFORMATION: Mytilus edulis

<400> SEQUENCE: 30
gcaaaaccgt cctaccctcc gacctataag                                        30

<210> SEQ ID NO 31
<211> LENGTH: 30
<212> TYPE: DNA
<213> ORGANISM: Artificial Sequence
<220> FEATURE:
<223> OTHER INFORMATION: Mytilus edulis

<400> SEQUENCE: 31
gctaaaccga gttacccccc gacttacaaa                                        30

<210> SEQ ID NO 32
<211> LENGTH: 20
<212> TYPE: DNA
<213> ORGANISM: Artificial Sequence -continued

```
<220> FEATURE:
<223> OTHER INFORMATION: primer

<400> SEQUENCE: 32
aattaaccct cactaaaggg                                              20

<210> SEQ ID NO 33
<211> LENGTH: 22
<212> TYPE: DNA
<213> ORGANISM: Artificial Sequence
<220> FEATURE:
<223> OTHER INFORMATION: primer

<400> SEQUENCE: 33
gtaatacgac tcactatagg gc                                           22

<210> SEQ ID NO 34
<211> LENGTH: 26
<212> TYPE: DNA
<213> ORGANISM: Artificial Sequence
<220> FEATURE:
<223> OTHER INFORMATION: primer

<400> SEQUENCE: 34
cctaacatat gggggttctc atcatc                                       26

<210> SEQ ID NO 35
<211> LENGTH: 22
<212> TYPE: DNA
<213> ORGANISM: Artificial Sequence
<220> FEATURE:
<223> OTHER INFORMATION: primer

<400> SEQUENCE: 35
atccgccaaa acagccaagc tt                                           22
```